(12) United States Patent
Lee et al.

(10) Patent No.: US 12,326,423 B2
(45) Date of Patent: Jun. 10, 2025

(54) COMPUTER-IMPLEMENTED PROCESSING OF SOUND WAVE SIGNALS FOR NON-DESTRUCTIVE EVALUATION OF WOODEN SPECIMEN

(71) Applicant: Volt Holdings Limited, Auckland (NZ)

(72) Inventors: Yishi Lee, Littleton, CO (US); Wayne Hall, Denver, CO (US); Dion Hall, Canberra (AU)

(73) Assignee: INNER VIEW TECHNOLOGIES LP, Auckland (NZ)

( * ) Notice: Subject to any disclaimer, the term of this patent is extended or adjusted under 35 U.S.C. 154(b) by 366 days.

(21) Appl. No.: 17/899,981

(22) Filed: Aug. 31, 2022

(65) Prior Publication Data

US 2023/0066782 A1 Mar. 2, 2023

Related U.S. Application Data

(60) Provisional application No. 63/239,035, filed on Aug. 31, 2021.

(51) Int. Cl.

| G01N 29/11 | (2006.01) |
|---|---|
| G01N 29/04 | (2006.01) |
| G01N 29/07 | (2006.01) |
| G01N 29/46 | (2006.01) |
| G01N 33/46 | (2006.01) |

(52) U.S. Cl.
CPC ........... *G01N 29/043* (2013.01); *G01N 29/07* (2013.01); *G01N 29/11* (2013.01); *G01N 29/46* (2013.01); *G01N 33/46* (2013.01)

(58) Field of Classification Search
CPC ...... G01N 29/043; G01N 33/46; G01N 29/07; G01N 29/46; G01N 29/11; G01N 2291/0289; G01N 2291/2634; G01N 2291/0238
See application file for complete search history.

(56) References Cited

U.S. PATENT DOCUMENTS

| 6,276,209 B1 * | 8/2001 | Schafer | G01N 29/2493 73/598 |
|---|---|---|---|
| 2020/0340951 A1 * | 10/2020 | Al-Buraik | G01N 33/46 |

FOREIGN PATENT DOCUMENTS

CA 2415361 A1 * 1/2002

* cited by examiner

*Primary Examiner* — Jennifer Bahls

(57) ABSTRACT

The technology disclosed relates to systems, methods, and devices for non-destructive evaluation (NDE) of a wooden specimen. A computer-implemented method for non-destructive evaluation of a wooden specimen comprises receiving acoustic wave signal data from NDE of the wooden specimen; processing the acoustic wave signal data to determine signal characteristics, such as an arrival velocity and amplitude attenuation of an AW2 mode; determining, based in part on a characteristic of the AW2 wave, an estimated strength metric of the wooden specimen; and displaying, on a graphical user interface associated with the computing device, an indication of the estimated strength metric of the wooden specimen.

20 Claims, 19 Drawing Sheets a) Test for the sectional plane b) Orientation of localized defect and plane wave response

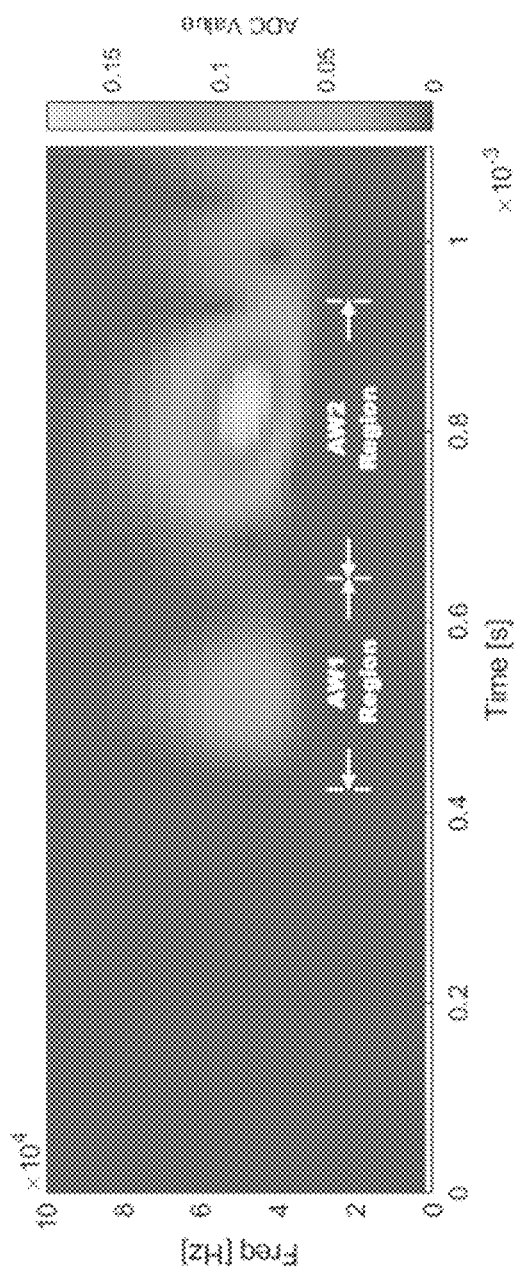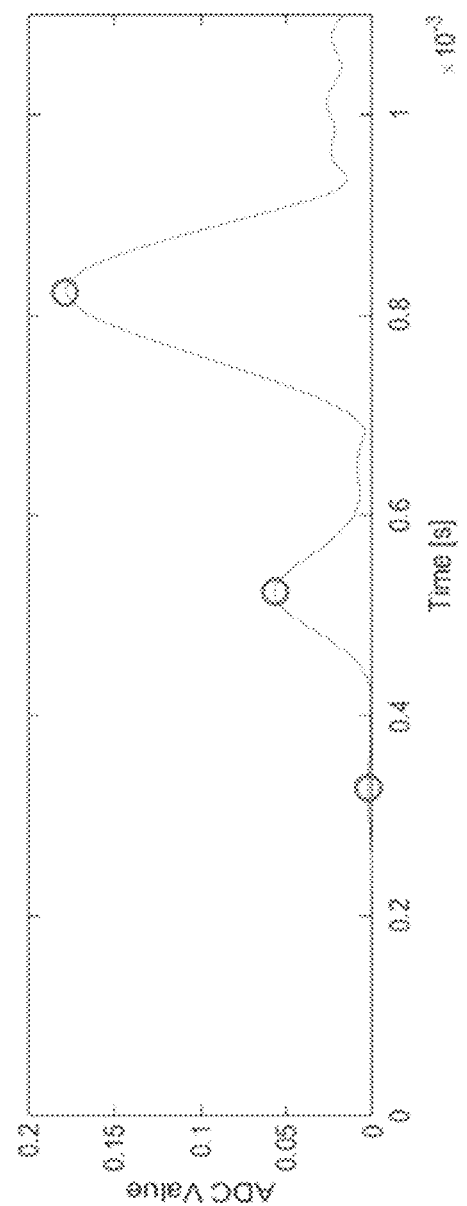
FIG. 5A
FIG. 5B

Setup of the static break test

Setup of the compression test

Result from the Linear Scattered Interpolator, R denotes the radial direction and θ denotes the tangential direction.

Propagation Velocity square of the Rayleigh mode vs. the fiber strength at the rupture location.

Attenuation Coefficient α of AW2 vs. Fiber Strength at the Rupture Location.

Attenuation coefficient α vs. the % remaining fiber strength.

TABLE I
SAMPLE SET FOR $t_9$ DETERMINATION.

| ACL | CIr | ENC of AW2 |
|---|---|---|
| 24 | 4772 | 1015 |
| 48 | 4688 | 1499 |

FIG. 16A

TABLE II
LINEAR AVERAGE CORRELATION COEFFICIENT OF DIFFERENT ANALYSES IN
RELATION TO DIFFERENT POLE GROUPS. $v$ AND $a$ DENOTE THE AVERAGE
PROPAGATION VELOCITY AND THE ATTENUATION COEFFICIENT
RESPECTIVELY.

| Analysis | 30-35 | 40 | 50-55 | Overall |
|---|---|---|---|---|
| $v^2$ - FB | 0.62 | 0.47 | 0.75 | 0.54 |
| $v^2$ - %RFS | 0.56 | 0.30 | 0.94 | 0.55 |
| $v^2$ - %RS | 0.49 | 0.18 | 0.66 | 0.53 |
| $a$ - %FB | 0.19 | 0.55 | 0.11 | 0.10 |
| $a$ - %RFS | 0.23 | 0.76 | 0.11 | 0.20 |
| $a$ - %RS | 0.20 | 0.79 | 0.16 | 0.23 |

FIG. 16B

Correlation between the AW2 velocity square and ACS values

COMPUTER-IMPLEMENTED PROCESSING OF SOUND WAVE SIGNALS FOR NON-DESTRUCTIVE EVALUATION OF WOODEN SPECIMEN

CROSS-REFERENCE TO RELATED APPLICATION

The present application claims priority to U.S. Provisional Patent Application No. 63/239,035 filed on Aug. 31, 2021 which is hereby incorporated herein by reference in its entirety.

TECHNICAL FIELD

The present disclosure relates to devices, systems, and methods capable of producing and receiving acoustic signals relating to non-destructive evaluation (NDE), where the acoustic signals may be utilized to assess structural integrity of a wood specimen, among other types of analysis.

BACKGROUND

The aging infrastructure power distribution grids across the world demand a rigorous and an objective monitoring process to assess structural integrity of hundreds of millions of wooden utility poles. Current inspection methodologies are antiquated and either lack the ability to provide truly accurate evaluations and/or result in compromising the structural integrity of a utility pole. For instance, one commonly used method of evaluating utility poles is an inspectors' visual evaluation of the pole. Visual inspection may be able to identify some structural integrity issues but is not a true indicator of whether the utility pole is experiencing incipient decay internally. As an example, a utility pole may appear to be fine and receive a passing grade upon a visual inspection, but internal decay may significantly affect the longevity of the pole, sometimes cutting its lifetime by decades. As there may be long gaps between the times when a utility pole is inspected, it is paramount to accurately assess the structural integrity of the utility pole.

Alternative measures for inspecting utility poles include drilling into the utility pole and testing a wood sample from its core. While this may provide more a reliable indication of whether a utility pole is experiencing decay, as compared with visual inspection, drilling into the core of a utility pole compromises the structural integrity of the pole. For instance, utility poles are coated with a protective layering that helps minimize exposure to elements that hasten decay. If this protective layering is compromised, decay may accelerate due to exposure to elements of nature, bacteria, etc.

Additional concerns exist when new technology is integrated in a field that commonly uses such antiquated methods to evaluate structural integrity. For instance, usage of complex electronic equipment may pose training challenges for inspectors and result in human error during actual operation. Additionally, signal data that may be initially collected during an inspection does not directly translate into meaningful information that an inspector can utilize to truly assess the structural integrity of a wooden specimen. Technical challenges are posed when contemplating how to decode waveforms of signal data to obtain important parameters for interpreting a physical structure of a specimen. As such, inspectors often rely on subjective assessment of the structural integrity by an inspector, thereby decreasing the likelihood of an accurate assessment. In most technical instances, inspectors are not trained to analyze signal data. This makes it nearly impossible to obtain real-time (or near real-time) assessments regarding condition a single wooden specimen, let alone a network of wooden specimens.

For these and other reasons, the present disclosure is presented to greatly advance the technical field of testing of structural integrity of wooden specimen including wooden utility poles.

SUMMARY

In view of the foregoing technical challenges, non-limiting examples of the present disclosure describe systems methods and devices for non-destructive evaluation (NDE) of a wooden specimen. According to a first example, a computer-implemented method for non-destructive evaluation (NDE) of a wooden specimen is provided. The computer-implemented method comprises: receiving, by a computing device, acoustic wave signal data from NDE of the wooden specimen; determining a velocity of an AW2 wave of the acoustic wave signal data; determining, based at least in part on the determined velocity of the AW2 wave, an estimated fiber strength of the wooden specimen; and displaying, on a graphical user interface associated with the computing device, an indication of the estimated fiber strength of the wooden specimen.

In another example, another computer-implemented method for non-destructive evaluation (NDE) of a wooden specimen is provided. The computer-implemented method comprises: receiving, by a computing device, acoustic wave signal data from NDE of the wooden specimen; processing the acoustic wave signal data with the computing device; determining an attenuation value of the wooden specimen based on the processing; determining, based at least in part on the determined attenuation value of the wooden specimen, an estimated fiber strength of the wooden specimen; and displaying, on a graphical user interface associated with the computing device, an indication of the estimated fiber strength of the wooden specimen.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIGS. 5A and 5B illustrate a time-frequency representation of time-series analog to-digital signals and energy response of the digital signals during NDE testing of a wooden specimen.

FIG. 16A is table of intensity levels for an arbitrary pole.

FIG. 16B is a table results of correlation analyses for propagation velocity or attenuation coefficient and various strength performance metrics.

DETAILED DESCRIPTION

Non-limiting examples of the present disclosure describe systems, methods, and devices for non-destructive evaluation (NDE) of a wooden specimen. According to a first example, a computer-implemented method for non-destructive evaluation (NDE) of a wooden specimen is provided comprising: receiving, by a computing device, acoustic wave signal data from NDE of the wooden specimen; determining a velocity of an AW2 wave of the acoustic wave signal data; determining, based at least in part on the determined velocity of the AW2 wave, an estimated fiber strength of the wooden specimen; and displaying, on a graphical user interface associated with the computing device, an indication of the estimated strength of the wooden specimen.

In another example, another computer-implemented method for non-destructive evaluation (NDE) of a wooden specimen is provided comprising: receiving, by a computing device, acoustic wave signal data from NDE of the wooden specimen; processing the acoustic wave signal data with the computing device; determining an attenuation value of the wooden specimen based on the processing; determining, based at least in part on the determined attenuation value of the wooden specimen, an estimated strength of the wooden specimen; and displaying, on a graphical user interface associated with the computing device, an indication of the estimated fiber strength of the wooden specimen.

Figure 1:
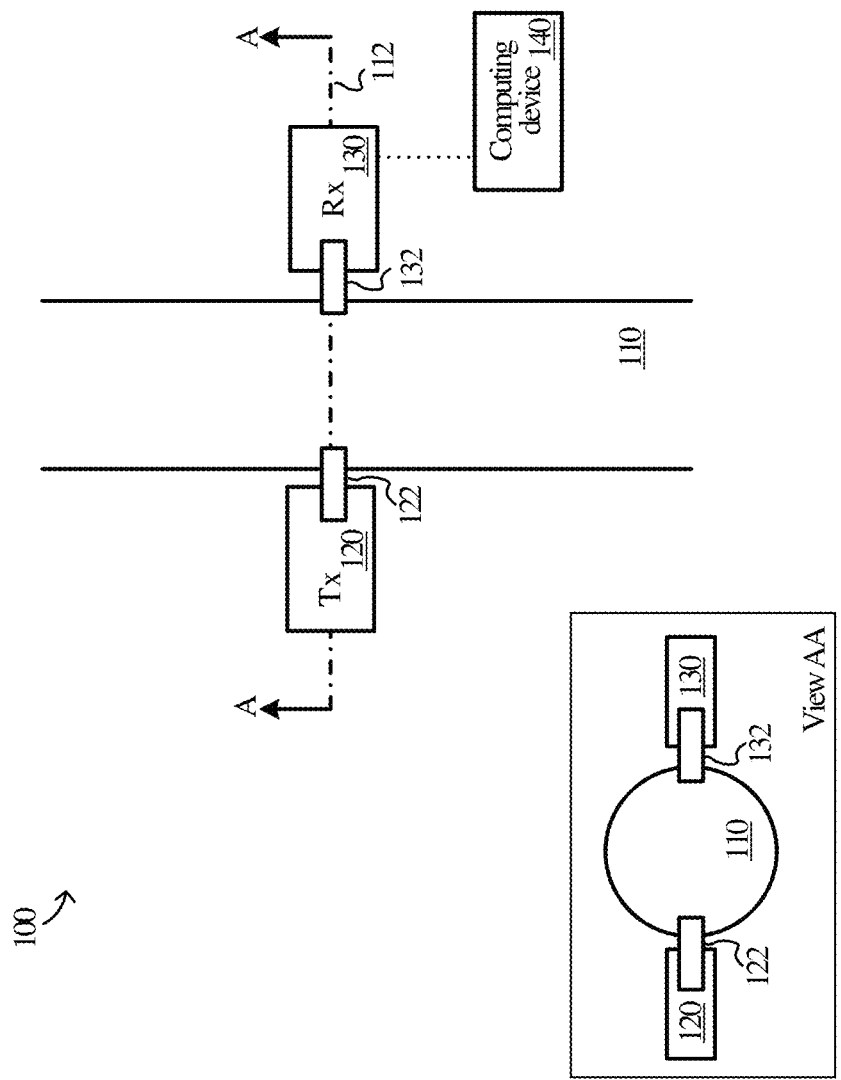
FIG. 1 illustrates an operational architecture for performing NDE of a wooden specimen in an implementation.

FIG. 1 illustrates operational architecture 100 of a system for performing NDE of a wooden specimen in an implementation. Operational architecture 100 comprises acoustic wave transmitter 120, acoustic wave receiver 130, and computing device 140 operatively coupled at least to acoustic wave receiver 130. Acoustic wave transmitter 120 and acoustic wave receiver 130 are coupled to waveguides 122 and 132, respectively, which are embedded in wooden specimen 110 and by which an acoustic wave, such as an ultrasonic pulse or signal, is transmitted through specimen 110. In an implementation, waveguides 122 and 132 are embedded in specimen 110 at diametrically opposite positions in propagation plane 112 comprising a cross-section of specimen 110. For example, for NDE of a vertical utility pole, waveguides 122 and 132 may be positioned one foot above the ground on opposite sides of the pole.

Computing device 140 comprises one or more processors operatively coupled to computer readable storage media and program instructions stored on the computer readable storage media which, when executed by the one or more processors, direct computing device 140 to perform the processes described herein. In an implementation, the program instructions direct computing device 140 to receive an indication of signal transmission from acoustic wave transmitter 120, to receive signal data from acoustic wave receiver 130, and to process the signal data to determine one or more acoustic wave characteristics relating to one or more physical characteristics of specimen 110. In an implementation, computing device 140 may be onboard acoustic wave receiver 130. In an implementation, computing device 140 may be operatively coupled to acoustic wave transmitter 120 to detect signal initiation. In an implementation, computing device 140 comprises program instructions which direct an onboard processing system to process the signal data including analog-to-digital conversion of the signal data. Processing may further comprise generating a time-frequency (TF) representation of the digitized acoustic signal.

Specimen 110 may comprise a wooden pole, such a utility pole, but may also comprise other types of structural elements, such as pilings, beams, or logs, or trees or standing timber. Although shown in a vertical orientation in operational architecture 100, it may be appreciated that the systems and methods for NDE of specimen 110 are applicable to wooden structural elements regardless of their position or orientation.

Figure 2:
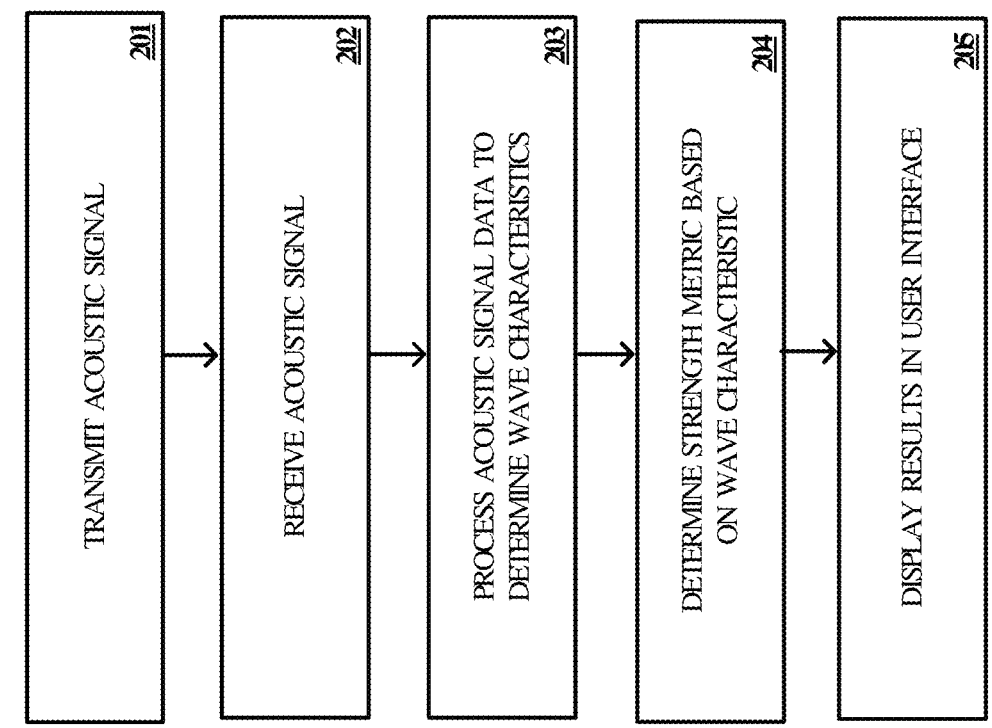
FIG. 2 illustrates an exemplary method of performing NDE of a wooden specimen in an implementation.
Figure 3:
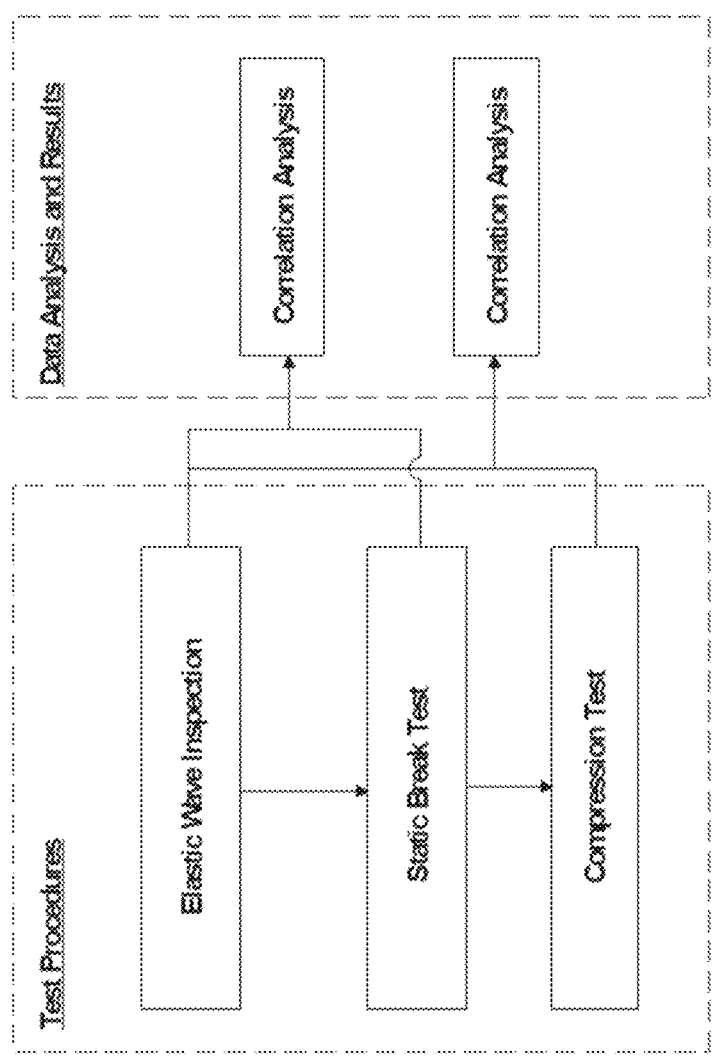
FIG. 3 illustrates an exemplary method of the test outlined in the description and the proposed analysis approach.
Figure 19:
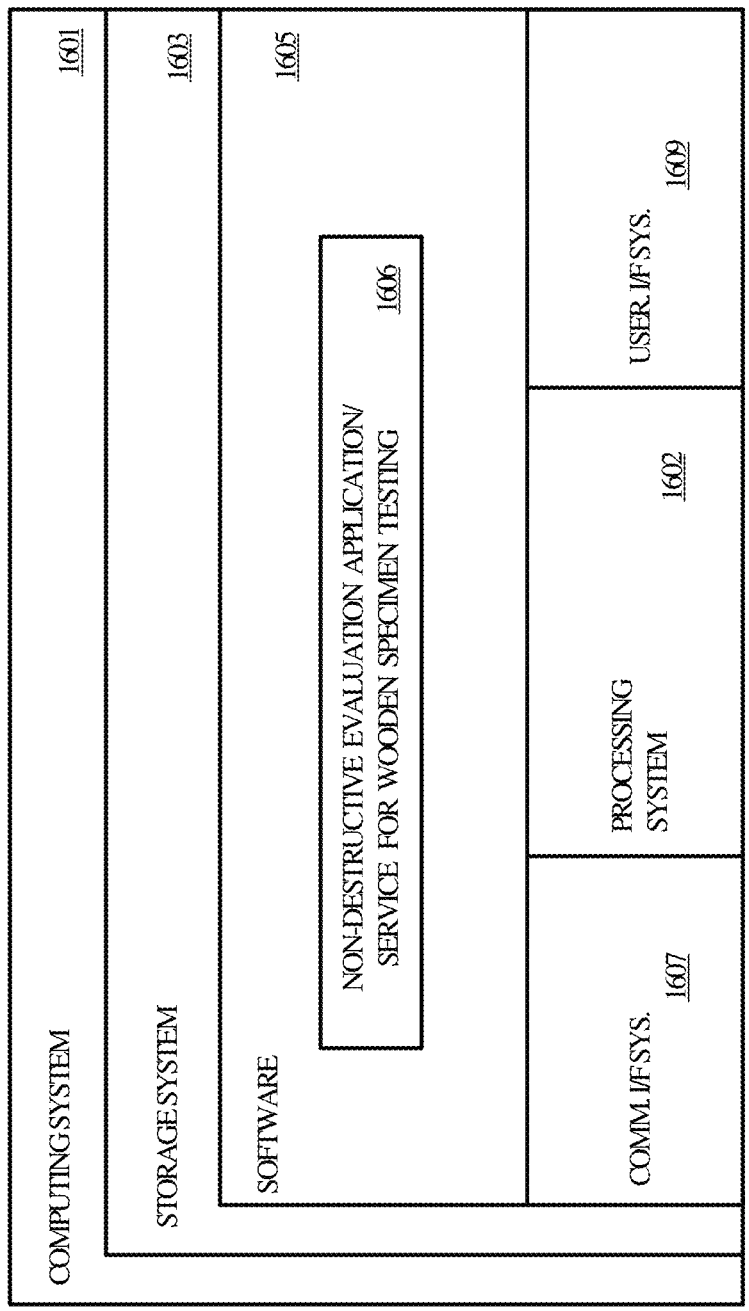
FIG. 19 illustrates a computing system suitable for implementing processing operations described herein related to NDE of a wooden specimen, with which aspects of the present disclosure may be practiced.

FIG. 2 illustrates process 200 for performing NDE of a wooden specimen implemented by a computing device, such as computing device 140 of FIG. 1 in an implementation. Process 200 may be implemented in program instructions in the context of any of the software applications, modules, components, or other such elements of a suitable computing device, of which computing device 1601 of FIG. 19 is representative. The program instructions direct the computing device to operate as follows, referring parenthetically to the steps in FIG. 2 and in the singular for the sake of clarity.

In operation, process 200 comprises transmitting an ultrasonic signal through the specimen by one ultrasonic transducer (step 201). In an implementation, the transmitted ultrasonic signal is a 50 kHz signal produced by an ultrasonic transducer. The transducer is physically connected to a waveguide which is embedded in the specimen such that the tip of the waveguide is pointed toward the center of the specimen. When the transducer produces an ultrasonic pulse or signal, the signal propagates outwardly from the tip of the waveguide through the specimen. The ultrasonic signal produces radial and circumferential Rayleigh modes which propagate through the specimen.

The ultrasonic signal is received by the second ultrasonic transducer which is operatively coupled to a computing device (step 202). The second transducer is physically coupled to a second (receiving) waveguide embedded in the specimen such that the tip of the waveguide is pointed toward the center of the specimen (and toward the transmitting waveguide) at the same vertical position of the transmitting waveguide. In an implementation, the second transducer detects the ultrasonic signal as it is received by a second (receiving) waveguide. In an implementation, both transducers act simultaneously as signal transmitters and receivers producing dual sets of signal data.

The computing device operatively connected to the second transducer processes the signal data to determine one or more characteristics of the acoustic signal (step 203). In various implementations, the computing device determines a propagation velocity and/or an attenuation value of the AW2 mode of the ultrasonic signal, wherein the AW2 mode comprises the circumferential Rayleigh mode of the acoustic wave corresponding to peak signal energy transmission. The computing device may also process the signal data to determine a time-of-flight, a signal intensity, and/or a peak energy of the AW2 mode of the ultrasonic signal.

In an implementation, processing the signal data includes performing an analog-to-digital conversion of the signal data and generating a time-frequency (TF) representation of the signal of the digital signal. The TF representation comprises quantifying signal energy as a function of signal frequency and time-of-flight (i.e., arrival time). From the processed signal data, a signal energy peak is identified which corresponds to the AW2 mode, including the energy and the arrival time of the AW2 mode. In various implementations, processing the ultrasonic signal data comprises using an analytic mother wavelet to represent the temporal waveform in the TF domain. In a preferred embodiment, processing the signal data may comprise a Gabor continuous wavelet transformation. The analytic mother wavelet may comprise Gabor wavelet, a Mexican hat wavelet, or a Cauchy wavelet.

In various implementations, processing the acoustic signal data comprises computing an average arrival velocity of the AW2 mode of the signal, wherein the average arrival velocity v comprises the circumference of the propagation plane C divided by the signal arrival time t at the energy peak, or:

$$v = C/t$$

The velocity v may be normalized to eliminate the dimensional dependency.

In various implementations, processing the acoustic signal data comprises computing an attenuation value based on the peak energy response, wherein the attenuation value corresponds to an attenuation coefficient $\alpha$ based on the intensity of the detected signal I, the initial intensity of the signal $I_0$, and the circumference of the propagation plane C according to:

$$\alpha = \frac{2 \ln (I_0/I)}{C}$$

In an implementation, the initial intensity of the signal $I_0$ may be extrapolated based on the energy response of an arbitrary pole based on above-ground measurements at two or more heights.

Wave interference occurs when an induced stress wave propagates within a small and confined area. The transducers produce the ringing effect, which further impedes an accurate calculation of the time of flight and peak energy. This can be resolved using a deconvolution process. In an implementation, the deconvolution process first identifies the point spread function from the impulse response of each arrival wave. Using a deconvolution inversion algorithm, corrupted signals of wider temporal spread are converted to a sharper ideal response. The result reduces the unwanted interference patterns, allowing AW2 to be identified more accurately.

The computing device determines various strength performance metrics of the specimen based on the one or more characteristics of the acoustic signal (step 204). In various implementations, the strength performance metrics of the wooden specimen include a fiber strength comprising a maximum structural strength of the specimen; a percentage of remaining fiber strength relative to a designed fiber strength; a percentage of remaining strength comprising the load at failure relative to the design load; and average shell compression strength.

Figure 10:
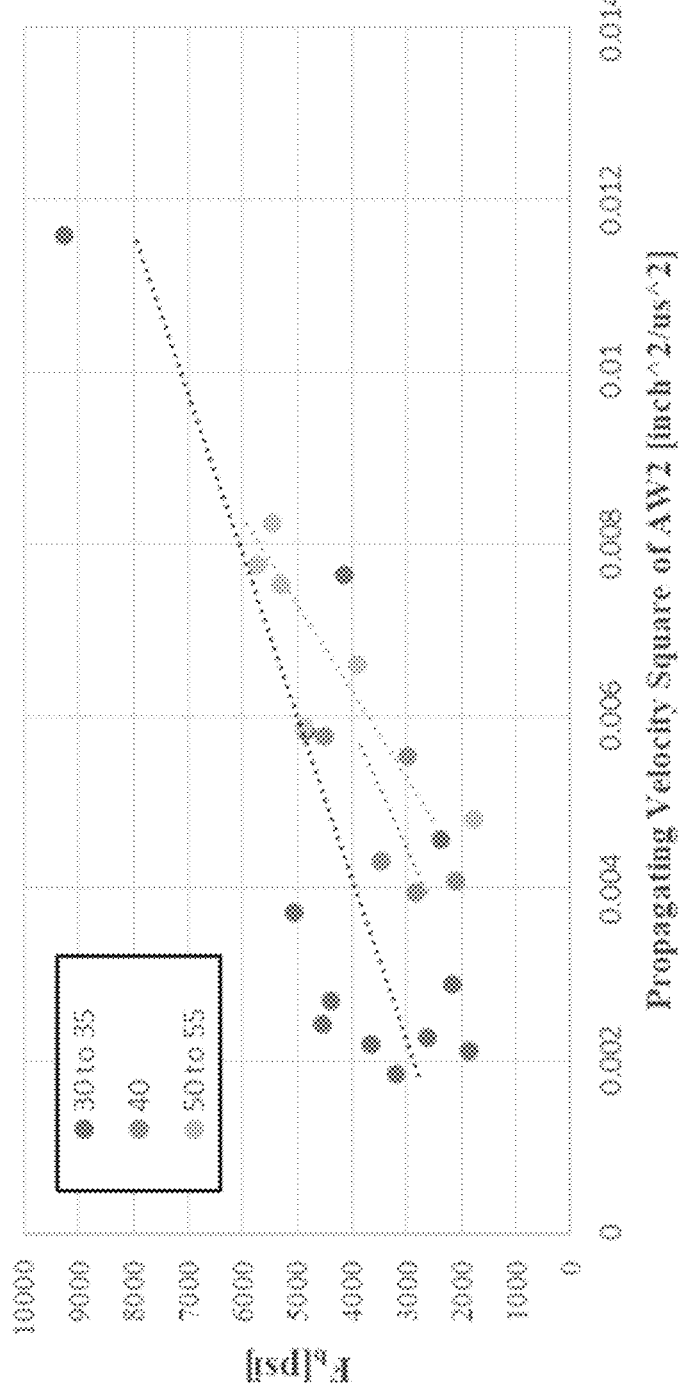
FIG. 10 is a graph of propagation velocity square of the Rayleigh mode vs. the fiber strength at the rupture location determined from NDE testing of wooden specimen.

In an implementation, the fiber strength $F_b$ of the specimen is determined based on a correlation to the square of the average arrival velocity v of AW2 wherein the correlation is based on empirical study. For example, FIG. 10 illustrates empirically determined correlations between $F_b$ and $v^2$ which vary with the length of the specimen.

Figure 11:
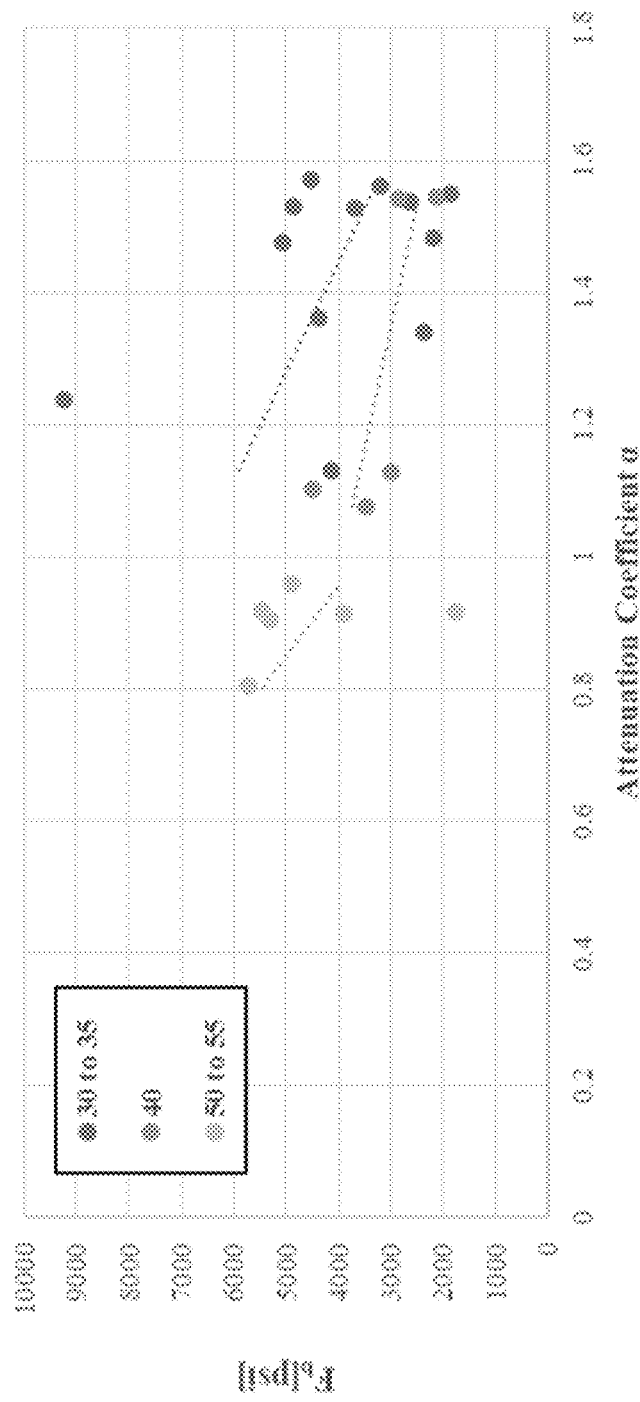
FIG. 11 is a graph of attenuation coefficient alpha of AW2 vs. fiber strength at the rupture location determined from NDE testing of wooden specimen.

Fiber strength $F_b$ may also be determined based on a correlation to the attenuation coefficient $\alpha$. Empirical measurements indicate that fiber strength $F_b$ varies inversely with the attenuation coefficient $\alpha$, wherein the correlation is based on empirical study. For example, FIG. 11 illustrates empirically determined correlations between $F_b$ and $\alpha$ which vary with the length of the specimen.

In an implementation, the strength performance of the specimen may be indicated by a percent of remaining fiber strength % RFS, which reflects an estimated fiber strength $F_b$ relative to a designed fiber strength $F_d$, or:

$$\% \ RFS = \frac{F_b}{F_d}$$

Figure 12:
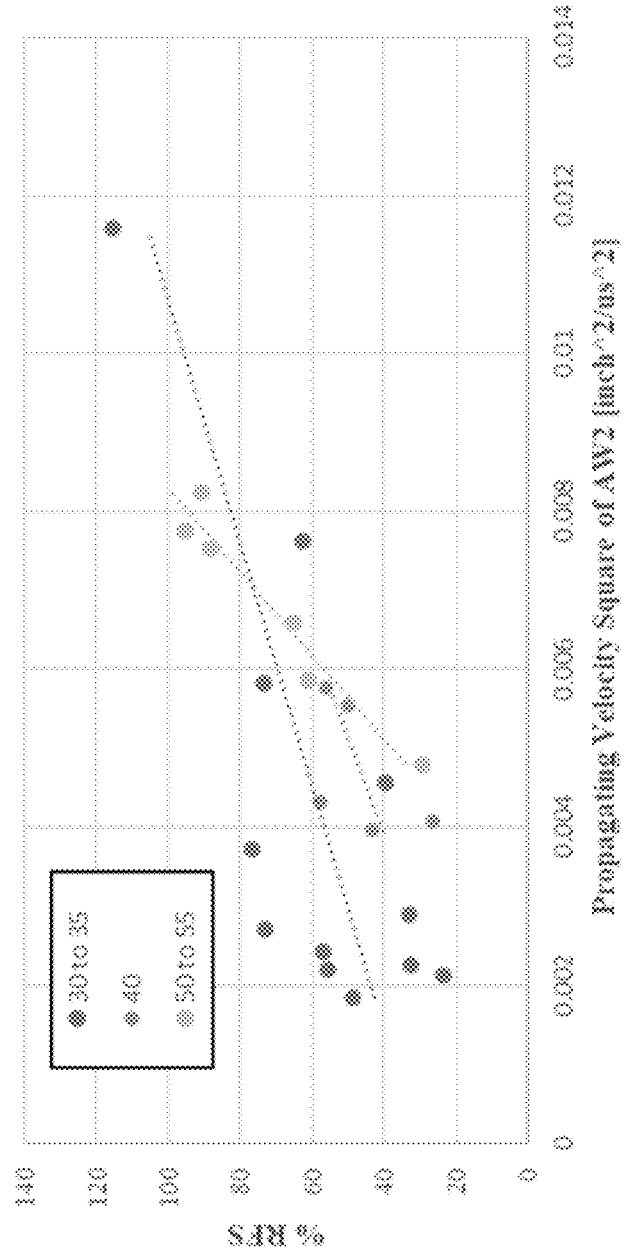
FIG. 12 is a graph of average propagation velocity square of the Rayleigh mode vs. the % remaining fiber strength determined from NDE testing of wooden specimen.

Percentage of remaining fiber strength % RFS may be determined based on a correlation to the square of the average arrival velocity v of AW2 wherein the correlation is based on empirical study. For example, FIG. 12 illustrates empirically determined correlations between % RFS and $v^2$ which vary with the length of the specimen.

Figure 13:
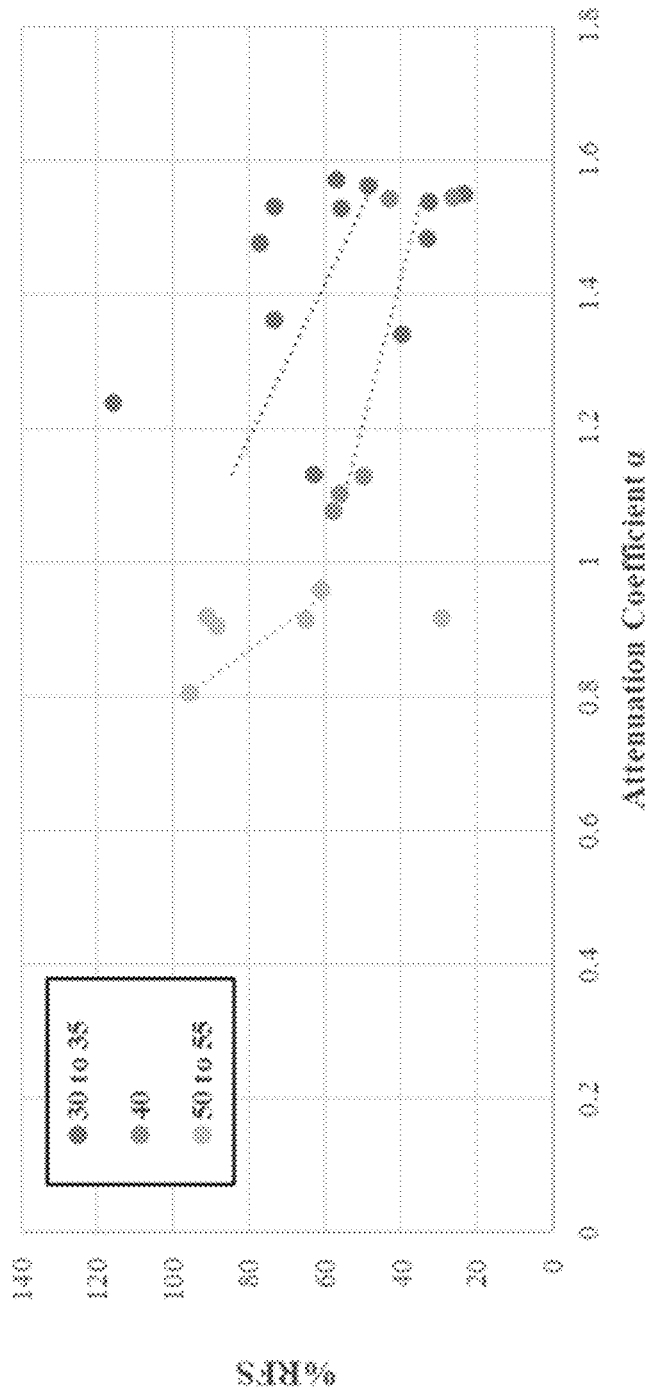
FIG. 13 is a graph of attenuation coefficient alpha vs. the % remaining fiber strength determined from NDE testing of wooden specimen.

Percentage of remaining fiber strength % RFS may be determined based on a correlation to the attenuation coefficient $\alpha$ wherein the correlation is based on empirical study. For example, FIG. 13 illustrates empirically determined correlations between % RFS and $\alpha$ which vary with the length of the specimen.

In an implementation, the strength performance of the specimen may be indicated by a percent of remaining strength % RS, which reflects an estimated load at failure P relative to a designed load or load capacity $P_d$, or:

$$\% \, RS = \frac{P}{P_d}$$

Figure 14:
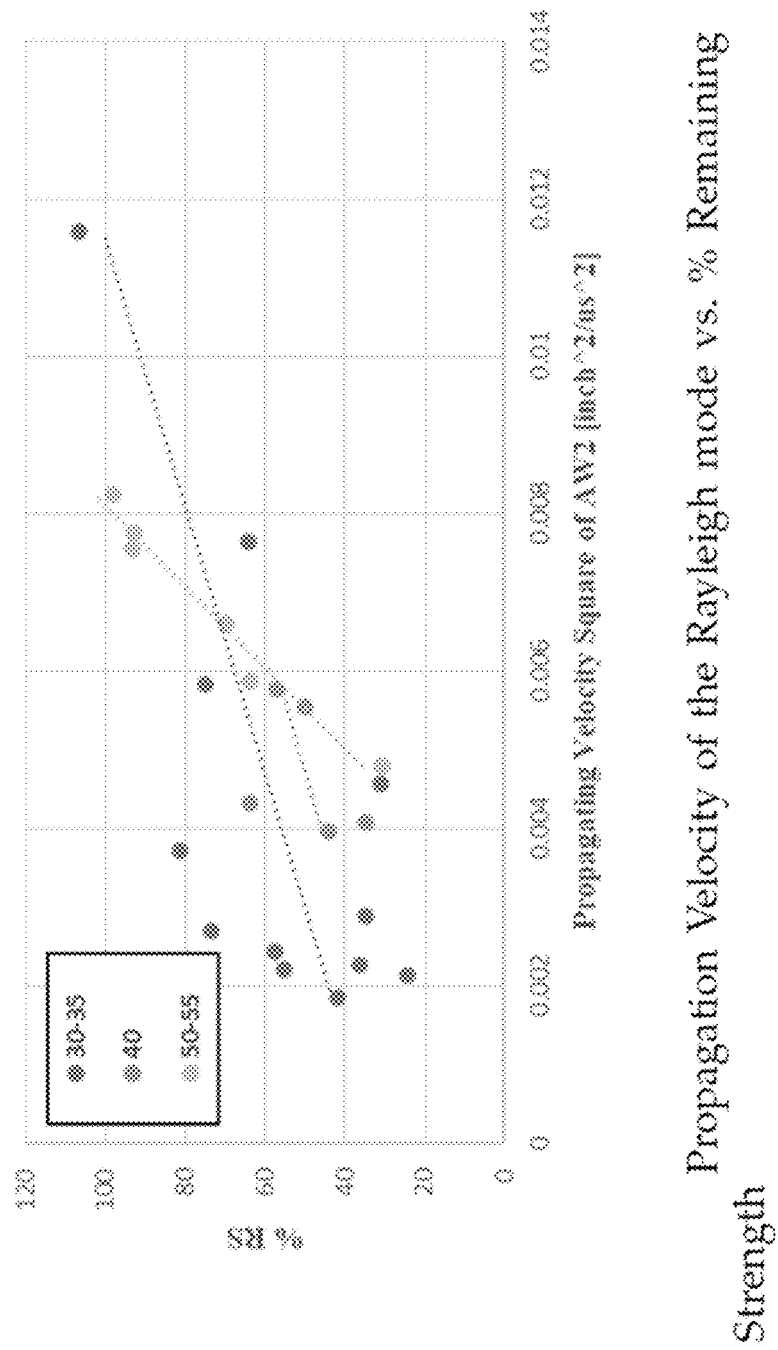
FIG. 14 is a graph of propagation velocity of the Rayleigh mode vs. % remaining strength determined from NDE testing of wooden specimen.

Percentage of remaining strength % RS may be determined based on a correlation to the square of the average arrival velocity v of AW2 wherein the correlation is based on empirical study. For example, FIG. 14 illustrates empirically determined correlations between % RS and $v^2$ which vary with the length of the specimen.

Figure 15:
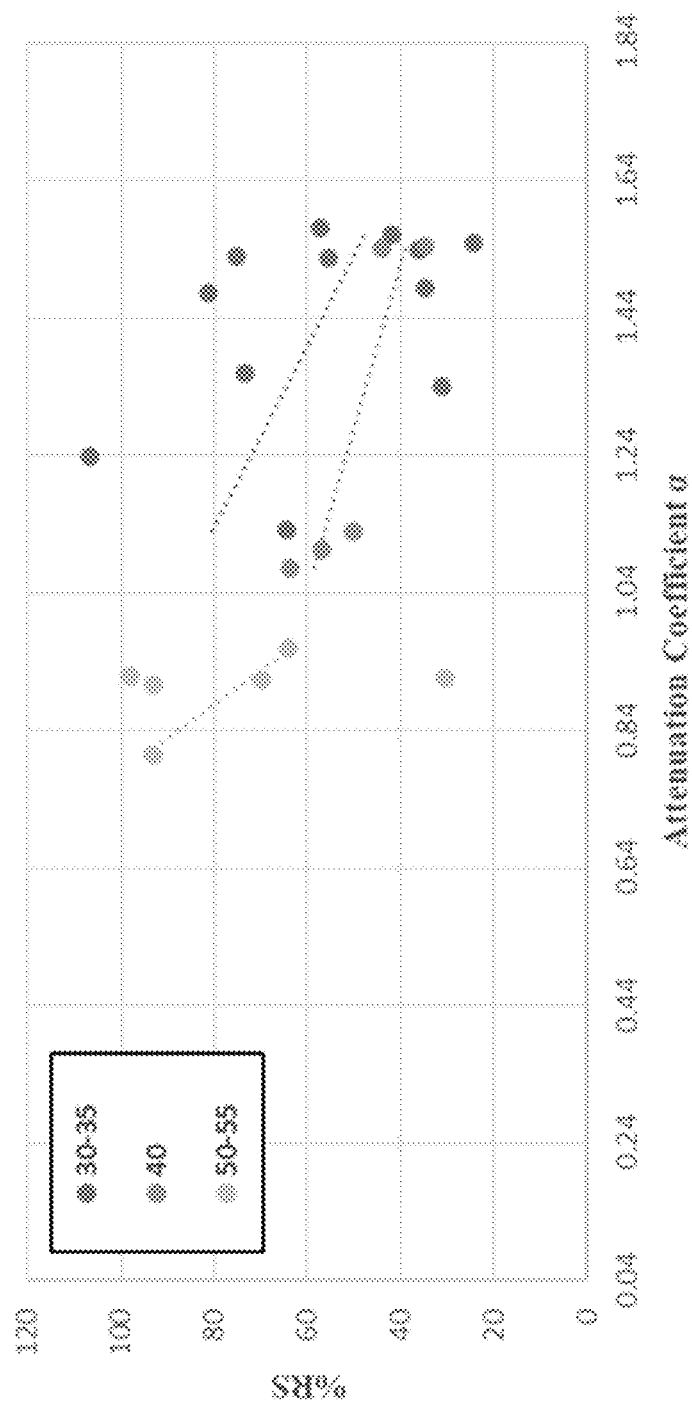
FIG. 15 is a graph of attenuation coefficient vs. % remaining strength determined from NDE testing of wooden specimen.

Percentage of remaining strength % RS may also be determined based on a correlation to the attenuation coefficient $\alpha$ wherein the correlation is based on empirical study. For example, FIG. 15 illustrates empirically determined correlations between % RS and $\alpha$ which vary with the length of the specimen.

In addition to varying with the length of the specimen, the correlations of fiber strength $F_b$, percentage of remaining fiber strength % RFS, and percentage of remaining strength % RS to the square of the arrival velocity $v^2$ of AW2 may vary with the circumference, age, and/or species of the specimen. Similarly, in addition to varying with the length of the specimen, the correlations of fiber strength $F_b$, percentage of remaining fiber strength % RFS, and percentage of remaining strength % RS to the attenuation coefficient $\alpha$ may vary with the circumference, age, moisture content, and/or species of the specimen.

In various implementations, the computing device receives additional data and determines one or more of the various strength performance metrics based on the additional data. For example, the additional data may comprise one or more physical dimensions of the wooden specimen, such as a length of the specimen or a circumference of a cross-section of the specimen. Additional data may also comprise information relating to the species of wood of the specimen. The computing device may also receive additional data relating to the age and/or moisture content of the specimen to be used in determining the various strength performance metrics.

The computing device displays, on a graphical user interface operatively coupled to the computing device, an indication of one or more of the various strength performance metrics, such as the estimated strength metric of the wooden specimen (step 205). For example, the user interface may display strength metric determined based on a correlation to a propagation velocity of an AW2 mode or an attenuation value of an AW2 mode, or both. In an implementation, the user interface may display a graphical TF representation of the acoustic signal similar to FIG. 5A or 5B.

In an implementation of the systems and methods for performing NDE of a wooden specimen described herein, the pair of waveguides are embedded at various longitudinal positions on a vertical specimen ranging from one foot below grade up to four feet above grade. In an implementation, two or more sets of signal data may be collected at waveguide positions at one-foot increments on the specimen.

For example, for a vertical pole specimen, the moisture content of the specimen may vary along the length of the pole. That is, the moisture content may be greater closer to the ground due to gravity. A higher moisture content may cause greater signal attenuation. To account for this effect, determining the strength performance metrics of the specimen may include using data relating to moisture content of the specimen, such as moisture content percentage, which in turn may be determined by comparing signal data from two vertical locations on the pole.

In an implementation of the systems and methods for performing NDE of a wooden specimen described herein, two or more sets of ultrasonic signal data are collected at a given cross-sectional or propagation plane of the wooden specimen. Subsequent to collecting a first set of signal data for the wooden specimen, a pair of waveguides is embedded at second positions in the specimen orthogonal to the first or original waveguide positions. (In other words, a line running through the second positions is orthogonal to a line running through the first or original waveguide positions.) A second ultrasonic signal is transmitted through the specimen from an ultrasonic transducer physically connected to one of the waveguides, and a second set of ultrasonic signal data is received by the second ultrasonic transducer connected to the other embedded waveguide.

Next, the signal data corresponding to the second ultrasonic signal is processed by the computing device to compare the AW2 mode of the second signal to the AW2 mode of the first signal to determine which of the signal data sets should be used to determine the various strength performance metrics of the wooden specimen. In an implementation, the computing device may compare a signal-to-noise ratio or a peak response energy of the first and second signal data sets to determine which signal data set will be used to determine the strength performance metrics. In various implementations, multiple sets of ultrasonic signal data are collected at two or more longitudinal positions of the specimen to obtain a more comprehensive understanding of the specimen's structural integrity.

In an implementation of the systems and methods for performing NDE of a wooden specimen described herein, processing the signal data further comprises determining characteristics of an AW1 mode of the acoustic signal, such as a propagation velocity, a time-of-flight, or an attenuation value. The velocity and amplitude attenuation values may be normalized to eliminate the dimensional dependency.

Ultrasonic-based nondestructive evaluation (NDE) has been employed in the utility sector to determine the cross-sectional groundline integrity of wooden utility poles. The technology disclosed herein teaches systems and methods for performing NDE of wooden utility poles and other wooden specimens based on the propagational characteristics of the ultrasonic stress wave using an embedded waveguide technique. The embedded waveguide technique excites diffusive Rayleigh mode of the AW2 wave ("AW2") which propagates in the shell region of the cross-sectional plane of a specimen. The employed Gabor wavelet transformation, and the model-based arrival region identification extract the propagation velocity and the associated spectral response of AW2. In an implementation, the technology disclosed herein uses static break assessment and longitudinal compression testing to quantify the cross-sectional strength of the test specimen. The technology comprises a comprehensive correlation analysis based on the extracted AW2 features and the associated destructive test. From previous test results, an overall correlation of $R^2$ ranging from 0.2 to 0.5 is achieved between the AW2 features and the static break test results, and an overall correlation of $R^2=0.4$ is achieved for 30 to 35-foot poles in the longitudinal compression test.

The propagating velocity determined via the mechanisms described herein is related to the mechanical property of the material (e.g., the wooden specimen), and the attenuation is a function of the porosity of the material. The velocity used in the waveform analysis described herein may be utilized to detect the expected arrival wave AW2. This wave mode propagates at the shell region of the pole, critical to the overall strength.

Acoustic signal energy is sensitive to the degradation of the wooden specimen. When the energy attenuation is determined accurately, it may be utilized to detect a change in porosity which can be used to indicate the early signs of decay. In some examples, the attenuation results may be hindered by the transmission and reception of energy of each ultrasonic probe being different. This may be corrected through an energy calibration process. In addition, moisture content of the specimen may affect attenuation of the signals. Examples described herein provide for estimating moisture content in a specimen by testing at a higher level above ground. Generally speaking, moisture does not go higher than one foot above the ground in a specimen. Examining the acoustic signal at least one foot above grade may mitigate the moisture effect and reduce false-positive results. If the moisture content of a sample can be estimated, this may provide an additional parameter to determine pole strength via the mechanisms described herein. For example, determining one or more strength performance metrics may comprise a two-dimensional correlation analysis in which attenuation and moisture content are independent variables (input) and a strength metric is the dependent variable.

In some examples, the models described herein may be adjusted or otherwise modified to account for moisture in a specimen. The described technique provides for performing measurements at a higher level (greater than one foot) above ground to mitigate the effect of moisture content in a specimen. Additionally, upon the moisture content of a specimen being accurately measured, the moisture content percentage may be factored into the model as an independent variable, making the estimated strength a function of both attenuation and moisture content.

In additional examples, the described systems, methods, and devices may incorporate specimen length in determining velocity and attenuation values to determine specimen strength. Longer specimens typically have large groundline circumferences compared to their shorter counterparts. To eliminate the dimensional dependency, the velocity and attenuation values may be normalized. This may be done by measuring the velocity of the stress wave rather than measuring the time-of-flight (TOF). The same scenario may be applied to the energy attenuation. Typically, attenuation also depends on the distance the acoustic wave travels. Therefore, the power model described herein may be utilized to eliminate the dimensional dependency by using the attenuation coefficient instead. Additionally, the mechanical property of wood varies with age. It can typically be assumed that larger specimens are produced from older trees, and smaller specimens are produced from younger trees. The mechanical properties in the shell region of younger and older trees can be different. Thus, different group lengths are included in the described plots to accommodate this difference.

The United States power and communication infrastructure relies on the structural integrity of approximately 154 million wooden utility poles. A reliable structural monitoring system is vital to ensure the sustainability of these networks. The traditional evaluation process has mainly relied on partial excavation, sound and bore techniques but the invasive nature can inadvertently damage the previously established internal chemical and physical characteristics of the poles. An incision in the wooden surface could negatively affect the strength in the cross-sectional plane. Additionally, an ANSI specification for new poles prohibits open or plugged holes. A number of comparison studies by U.S. utilities have indicated that ultrasonic nondestructive testing (NDT) can produce the same level of efficacy as the partial excavate, sound and bore process. Using time-frequency domain representation, critical parameters of a reflected stress wave can be extracted to characterize the material property.

The technology disclosed herein begins with an ultrasonic test in which a through-transmission stress wave signal is acquired using an acoustic wave device or ultrasonic transducer, such as the UB1000 device. The ultrasonic test is performed in the cross-sectional planes of the test specimen from 1 foot below grade up to 4 feet above grades with a 1-foot longitudinal increment. In an implementation, physics-based signal analysis technique of extracting vital information from the stress wave signal is performed on multiple poles. The poles are then subjected to the static break test in accordance with the ASTM 1036 Standard Test Method. The poles are then cut to a specific length in the longitudinal direction for the longitudinal compression testing. The results from the mechanical testing (static break test and the compression test) are examined against the stress wave signal.

Figure 4A:
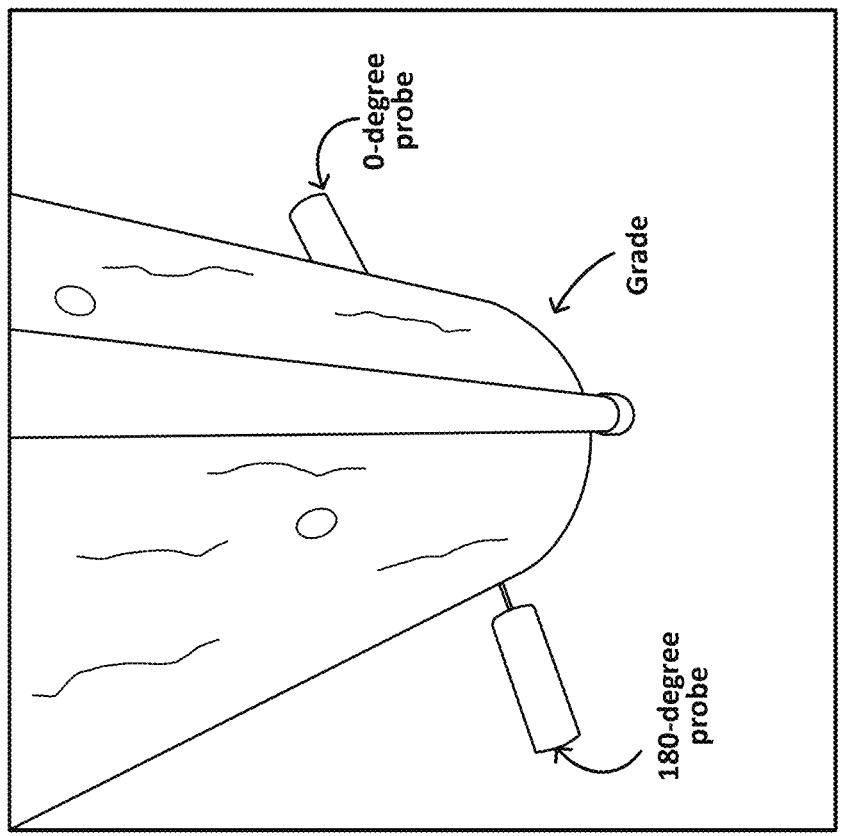
FIG. 4A illustrates an exemplary setup for NDE testing of a section plane of a wooden specimen.
Figure 4B:
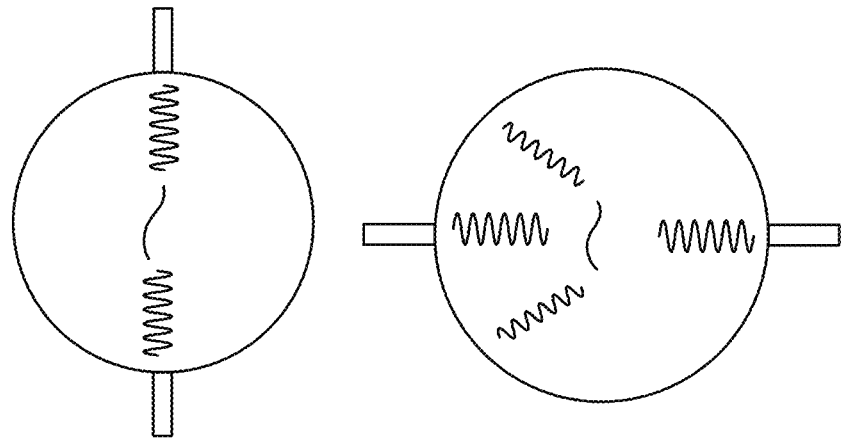
FIG. 4B illustrates the orientation of localized defect and plane wave response for NDE testing of a wooden specimen.

In an implementation, a sectional plane above grade is determined. An arbitrary 0-180 degree orientation is chosen as the reference points in the sectional plane as illustrated in FIG. 4A. Two embedded waveguides are inserted 15 mm into the medium to which ultrasonic transducers are attached. The same procedure is repeated for the 90-270 degree orientation. It has been observed that the two orientations can produce vastly different acoustic responses, primarily due to the orientation of the local imperfection in the sectional plane with respect to the direction of the traveling stress field. When the lengthwise direction of the imperfect is perpendicular to the propagation direction, strong reflection can occur, causing interference response and stronger attenuation at the receiving end. Likewise, when the lengthwise direction of imperfection is parallel to the propagation direction, the interaction is much weaker. This phenomenon is illustrated in FIG. 4B. Hence, the drastic difference in signals between the two orthogonal directions is an indication of a local imperfection. The two orientations are compared, and the highest signal-to-noise (SNR) is selected for analysis. When both orientations result in similar energy and temporal responses, it is often an indication of a global response of the sectional plane in question.

In an implementation, stress waves are produced by an acoustic device or probe, such as the UB1000 ultrasonic transducer, designed to generate a narrow-band radiation source of 50 kHz utilizing a high-power piezoelectric transducer. Custom circuitry in the probe produces high-voltage discharge and processes the received analog signal using an onboard analog-to-digital unit. The device is coupled to an embedded waveguide inserted into the wooden medium to produce radial and circumferential Rayleigh modes. The velocity and diffusive characteristics of the circumferential Rayleigh mode or the arrival mode number 2 (AW2) can characterize the material properties near the half-space boundary. The Rayleigh mode can be extracted from the complex stress wave response in the circular cross-sectional plane of the groundline region. Decay mechanisms occurring in the specimen typically contribute to the loss of porosities. The viscous damping coefficient of the displacement field depends strongly on the coupling factor which causes amplitude attenuation of the propagating stress wave. The energy propagation velocity responds strongly to the change of elastic moduli and density. Aggregated findings relating to signal amplitude attenuation and energy propagation velocity in a wooden medium inspire the use of an analytic wavelet to represent the temporal waveform in the time-frequency (TF) domain. This representation extracts the Rayleigh mode arrival along with the energy content.

Processing the signal data comprises, in an implementation, wavelet transformation which is based in part on selecting an operator function defined as the mother wavelet. The mother wavelet can take on different forms depending upon the application. To select a proper mother wavelet, signals containing dynamic frequency and time components should use analytic wavelet function (AWT) to analyze the signal. In contrast, non-analytic mother wavelets often lead to interference, and artifacts that can erroneously represent the amplitude and phase. Analytic mother wavelets such as the Gabor, the analytic form of the Mexican hat, and Cauchy may be used. The most proper wavelet tends to have a matched shape as the signal in question. Among the examined wavelets, the Gabor wavelet exhibits a temporal response similar to the transient waveform estimation by the dual waveguide configuration. The Gabor wavelet exhibits an acceptable frequency resolution for better spectral analyses and detection of the spectral response in the low-frequency region. The Gabor continuous wavelet transformation (CWT) produces a desirable temporal and spectral representation of the signal to detect the mechanical and the poroelastic variations in the propagating medium. This transformation suffers temporal resolution in that range, but it is a common drawback in any TF domain representation according to the uncertainty principle.

FIG. 5A depicts a TF representation of a time-series analog-to-digital (ADC) signal. Two pronounced clusters correspond to the energy arrival of AW1 and AW2 arrival regions as illustrated in FIG. 5A. Isolating the fundamental frequency of the received waveform yields the energy response in the temporal domain as illustrated in FIG. 5B. The peaks that are circled in FIG. 5B correspond to the arrivals of dominant energy propagation. The peak value provides both temporal information which can translate to the propagation velocity and the attenuation of the energy.

Using the proposed wavelet analysis technique, the extracted temporal-energy response in the signal can be examined. By discarding the effect of intermodal interference, the stress energy of the specific arrival mode dominates the energy contained within the selected arrival region. Hence, the peak energy is extracted to determine the Rayleigh mode propagation. Since the propagation plane has a dimensional variation based on the pole class and the tapering effect above grade, this variation is considered by computing the average propagating velocity with the corresponding circumference at the plane of propagation. That is, $$v = C/t$$

where C is the circumference of the propagation plane, t is the arrival time of the energy peak. In a linear viscoelastic solid such as wood, the inelastic scattering and the irreversible process attenuate the energy of the wave. Incipient decay contributes to an increase of porosity. To quantify the attenuation characteristics, peak energy response is used to extract the primary mode and the attenuation can be computed based on the power-law model:

$$I = I_0 e^{-\alpha x}$$

where $I_0$ is the initial intensity of the stress wave, I is the energy flux measured in an attenuating medium at a distance x from the source, and $\alpha$ is the amplitude attenuation coefficient. The power-law model describes the received energy intensity as a function of the initial wave intensity, propagation distance, and the attenuation coefficient. The attenuation coefficient strongly couples with the property of the medium. In turn, it provides the means to characterize the condition of the medium. Manipulating the power-law model yields an equation for the attenuation coefficient:

$$\alpha = \frac{2 \ln (I_0/I)}{C}$$

where C is the circumference of the sectional plane in question. $I_0$ may be determined by obtaining the energy response of an arbitrary pole with above-ground level measurements (AGL) at, for example, 24 and 48 inches (see Table I of FIG. 16). The tapering geometry of a pole generates two simultaneous equations for estimating $I_0$.

Figure 6:
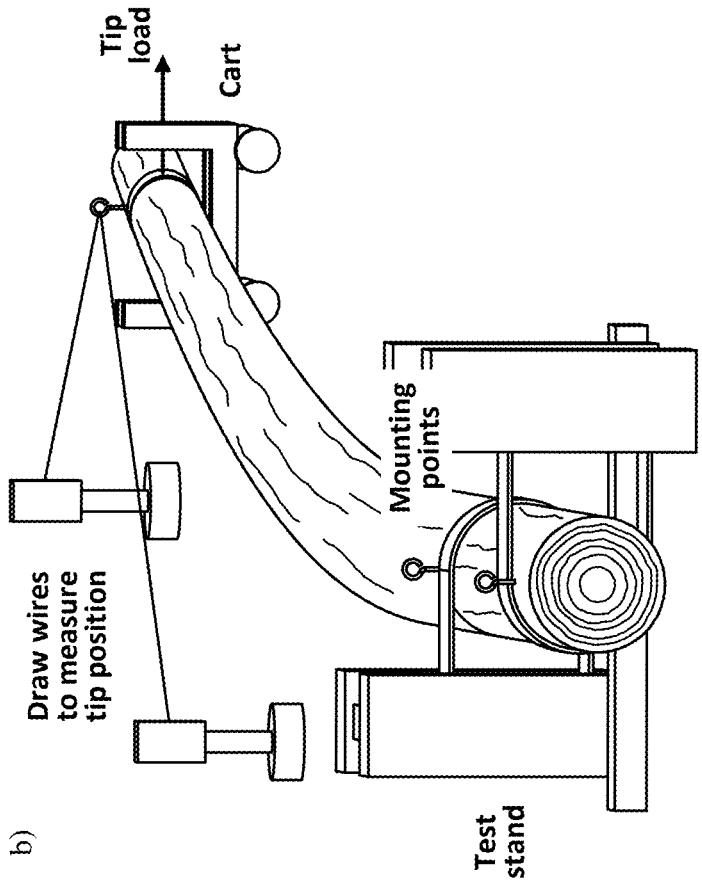
FIG. 6 illustrates an exemplary setup for NDE testing of a wooden specimen for a static break test.
Figure 6:
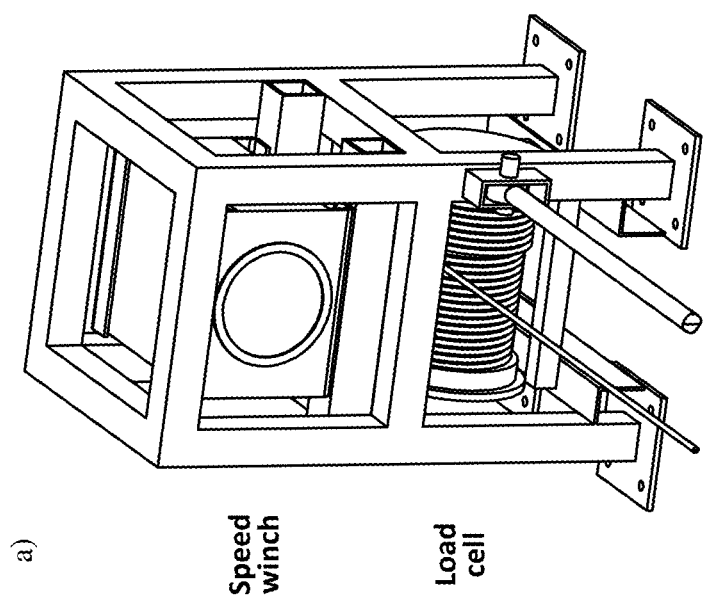

FIG. 6 illustrates a static break test setup in an implementation. A test specimen is restrained at the groundline and few inches above the bottom of the pole to simulate the ground support. A cart shown in photo (b) of FIG. 6 supports the tip of the pole to eliminate orthogonal load due to gravity. A tip load is applied to the cart using the variable speed winch until reaching the sufficient failureforce.

To measure the deflection, a system of four draw wire sensors measures the pole deflection. Two draw-wire sensors measure the movement 2 feet from the tip at the point of load application. Two draw-wire sensors measure the rotation or ground-line movement at the butt, allowing the exact measurement of the tip location with respect to the groundline. A load cell shown in photo (a) of FIG. 6 is mounted on the speed winch measures half of the applied load.

Based on the applied failure load of the static break testing and the measured deflection, an empirical value of the maximum fiber strength at the groundline can be calculated based on the following equation:

$$F_b = 32\pi^2 P(a - \Delta a)/C^2$$

where $F_b$ denotes the maximum fiber stress of the location of the plane of rupture (POR), P is the imposed failure tip load, a is the longitudinal distance between the load point and the break, and $\Delta a$ is the maximum longitudinal deflection.

During the static break test process, a test specimen is first rested on a test stand and restrained at the predetermined mounting points. Based on the specimen's pole class, the winch placement or the load point is determined. Each specimen is tested with a load applied at a constant rate. Simultaneously, the tip position is measured at a 10 Hz sampling rate. Once the testing is completed, the load and deflection measurements are used to determine the modulus of elasticity (MOE) and the modulus of rupture (MOR).

Figure 7:
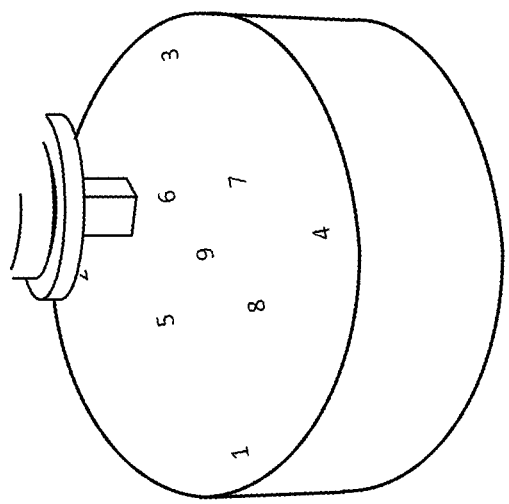
FIG. 7 illustrates an exemplary setup for NDE testing of a wooden specimen for a compression test.
Figure 7:
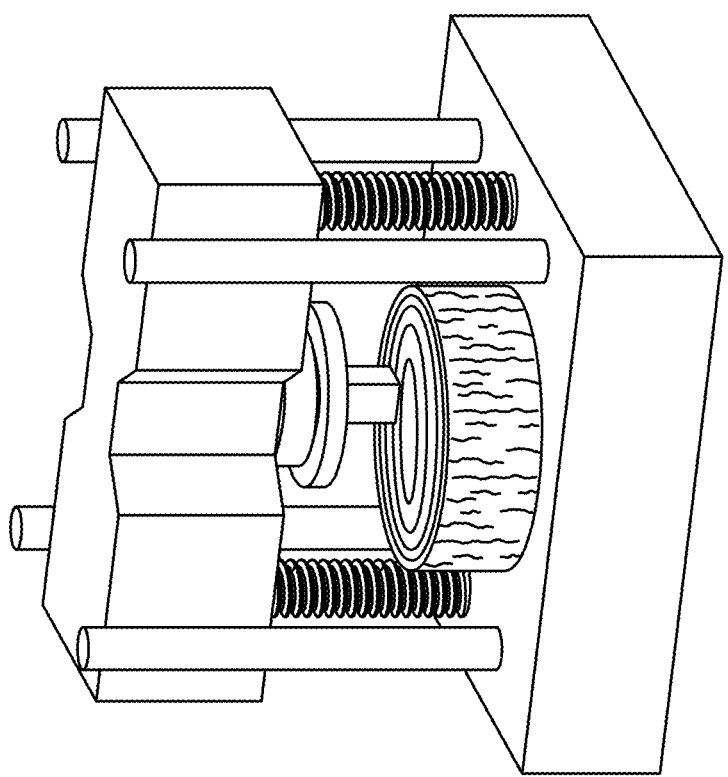
Figure 8:
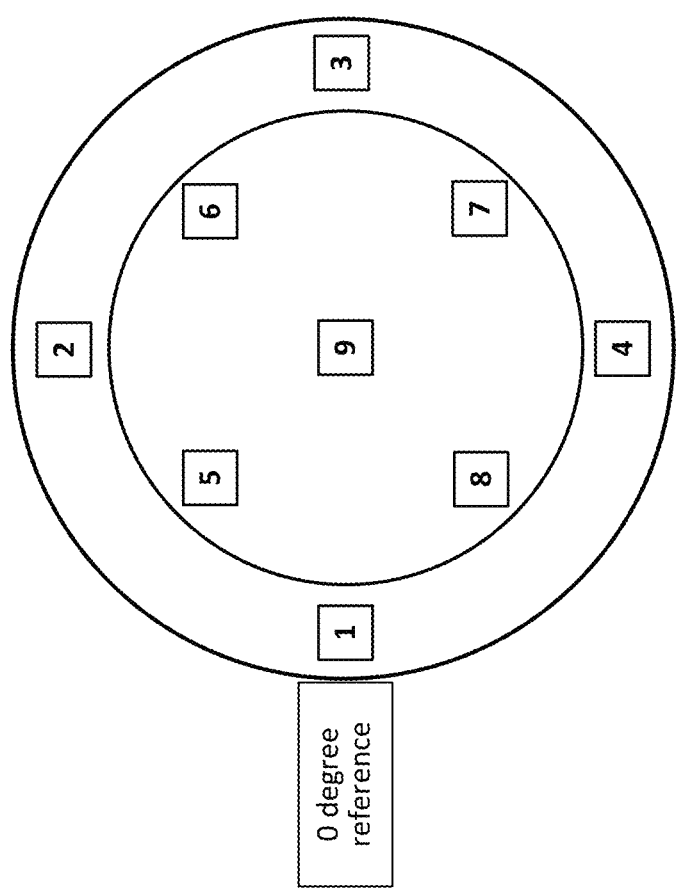
FIG. 8 is a diagram illustrating nine different points that are examined during NDE compression testing of a wooden specimen.

FIG. 7 illustrates a compression testing setup of a wooden specimen in an implementation. Because the rupture plane from the static break test produces an unsuitable surface for the longitudinal compression testing, a one-foot cylindrical specimen is cut at about one foot from the rupture plane to avoid altering a mechanical property. The prepared specimen is stored in a controlled environment with a temperature of 75 degrees C., relatively humidity of 50% for 43 days. The compression parallel to the grain procedure is done in accordance with the ASTM D 143-14 "secondary method." Using 1-inch by 1-inch square metal rod, the load is applied to the surface of specimens at a rate of 0.1 inches per minute until 0.1 inch is achieved. The load is recorded to calculate the corresponding compression stress. To the average response in both the shell and heart regions of the specimen, nine different points with 5 positioned in the heart region and 4 positioned in the shell region are examined, as illustrated in FIG. 8.

The structural strength performance of a specimen may be evaluated using the fiber strength at the rupture plane and the overall remaining strength of the pole. Each parameter is described separately below.

Fiber Strength and % Remaining Fiber Strength. The acoustic wave corresponding to peak energy is characterized by the average arrival velocity $v_{pe}$ and the energy attenuation coefficient $\alpha_{pe}$. To draw a correlation between the structural strength and the acoustic wave signal characteristics, the variation of different pole classes is normalized. Normalizing the variables eliminates variation introduced from different pole classes, effectively increasing the number of comparable samples for the correlation analysis.

The fiber strength measured at the break point may also be compared to the designed fiber strength to produce a percentage remaining fiber strength (% RFS):

$$\% \, RFS = \frac{F_b}{F_d}$$

where $F_b$ is the measured fiber strength and $F_d$ is the designed fiber strength based on Table 1 in ANSI 05.1. Percentage remaining fiber strength is a normalized quantity which can be used to estimate strength degradation of specimen.

Percentage Remaining Strength. The percentage remaining (% RS) defined by:

$$\% \, RS = \frac{P}{P_d}$$

where P is the load at failure and $P_d$ is the designed class tip load or maximum load capacity. The designed class tip bending capacity $\tau_{cap}$ is determined via following expression based on the ANSI 05.1:

$$\tau_{cap} = P_d L = k F_b C^3$$

where k is a conversion constant (k=0.000264), $F_b$ is the nominal fiber strength at the ground line, C is the ground line circumference, and L is the distance between the ground line and the load point. Based on the bending capacity, the maximum load capacity $P_d$ can be determined. As noted in ANSI 05.1, this calculation contains a coefficient of variation (COV) of approximately 20%.

Figure 9:
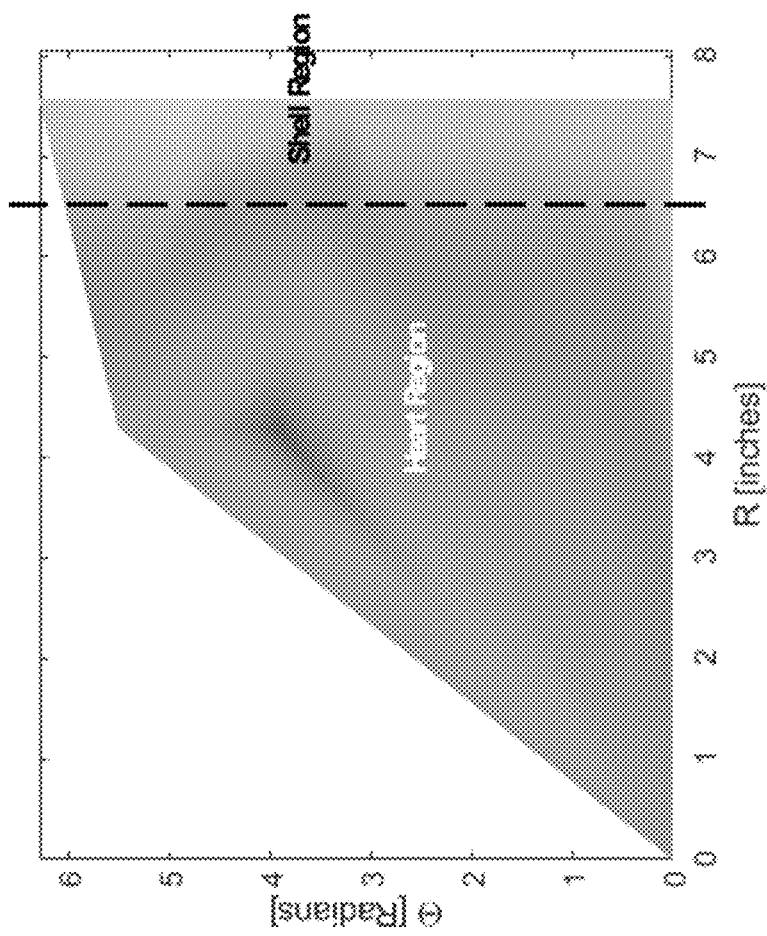
FIG. 9 is a graph illustrating results from a Linear Scattered Interpolator in NDE testing of a wooden specimen, where R denotes the radial direction and theta denotes the tangential direction.

Average Compression Shell Strength (ACS). Based on the compression test results, the assumed coordinate of the test points and the associated compression values are imported to a scatter interpolator to generate an overall response of the entire specimen. To prevent any unrealistic gradients in the overall compression response, a linear interpolator is used to produce $C^0$ continuity function resulting in a smooth distribution of compression results in the computational domain. To incorporate the orthotropic property of the cross-sectional plane, the proposed interpolation is performed in the polar coordinate system. An exemplary result is shown in FIG. 9. The ACS strength value is calculated using the root mean square compression value $x_{RMS}$ defined as:

$$x_{RMS} = \sqrt{\frac{1}{N} \sum_{n=1}^{N} |x_n|^2}$$

where N is the number of data points and $x_n$ are the compression values obtained from the linear interpolator at the selected shell region.

The results of mechanical testing and signal data collection suggest that the steady-state Rayleigh mode propagation is an aggregate motion of the fast and slow modes associated linearly with the phase velocity of the dilatational and distortional fields. The phase velocities suggest a linear relationship between the mechanical property and the velocity squared, thus, a linear model is used to perform data fitting and correlation analysis. Prior work in the art formulated the attenuation coefficient $\alpha$ of the poroelastic wave as a viscous damping term which varies linearly with material loss. By combining the viscous damping model with the power-law model discussed above, a logarithmic model can be assumed to analyze the correlation relationship between the energy attenuation and the mechanical property.

Rayleigh Mode (AW2) Response to Fiber Strength. Sectional measurements using an ultrasonic transducer are performed prior to the static break test at 0, 12, 24, 36, and 48 inches above the ground line plane. Each cross-sectional measurement is termed the plane of measurement (POM). The AW2 is then extracted, and the obtained average velocity and the energy response are compared with the strength performance metrics. After the proposed static break test on the entire sample set is performed, the location of POR is measured. Poles with a POR value within 3 inches of the POM are selected. This approach assumes minimal property variation in the longitudinal direction.

Twenty-three poles are selected for use in the analysis based on the proximity of the POM to the POR. Within this sample set, the sample poles are from a diverse population of species ranging from 30 feet to 55 feet. The samples are grouped based on the lengths to determine if the age of the pole impacts stress wave characteristics. The average velocity and the attenuation coefficient are depicted in FIGS. 10 and 11. FIG. 10 compares the average propagating velocity squared at the POM to the fiber strength at the POR. Using the linear regression model, the three groups, 30-35, 40, and 50-55, exhibit three different correlations with the highest correlation in the 50-55 group. All groups suggest a directly proportional linear correlation between the squared average velocity and the fiber strength. The average correlation coefficient across all length groups is 0.54.

FIG. 11 compares the attenuation coefficient $\alpha$ with the fiber strength at the POR. The energy response yields a smaller correlation coefficient compared to the average velocity depicted in FIG. 10. Two distinct clusters are formed among the three different length groups. By eliminating the spatial dependency using the power-law model, the result suggests that the larger class poles with greater groundline circumferences tend to have a smaller attenuation coefficient than the smaller class poles with smaller groundline circumference. This finding is pronounced between length group 30-35 and length group 50-55. By discarding the outliers, the fiber strength exhibits an inversely proportional relationship with the attenuation coefficient. This result suggests that wood fiber with a stronger fiber strength tends to have less wave energy attenuation than fiber exhibiting weaker strength. Across all length groups, the overall correlation coefficient is 0.1.

Rayleigh Mode (AW2) Response to the % Remaining Fiber Strength. The analyses of the % remaining fiber strength and AW2 response characteristics are depicted in FIGS. 12 and 13. In FIG. 12, the result yields three different correlation values for the length groups. This result suggests the correlation can be improved by individually considering each length group. The overall correlation coefficient is 0.55, slightly stronger than the fiber strength comparison ($R^2=0.54$). As described above, the % RFS reflects the property degradation from the nominal designed strength, making this analytical technique more valuable than the fiber strength comparison.

FIG. 13 shows two distinct clusters. The length group of 50-55 has a relatively lower attenuation coefficient than the length groups of 30-35 and 40. This finding resonates with the finding suggested in FIG. 11. This result suggests that the differences in fibril structure between the different length groups need to be considered when considering the correlation between a and % RFS. The group-specific correlation coefficients suggest that the % RFS has a higher correlation to the attenuation than the fiber strength. This result also yields an overall correlation coefficient of 0.2, a 100% increase compared to the average correlation coefficient calculated above. The overall inversely proportional relation indicates that the attenuation coefficient increases with decreasing % RFS, supporting the hypothesis that mechanical property degradation attenuates wave energy.

Rayleigh Mode (AW2) Response to the % Remaining Strength. % RS indicates the overall structural integrity at the load point based on the groundline strength assessment. The related results are depicted in FIGS. 14 and 15. FIG. 14 compares the propagating velocity against the % RS. The $R^2$ result indicates a slightly weaker correlation than the analyses comparing the fiber strength and the % RFS. Nevertheless, this result suggests a directly proportional relationship between the average propagating velocity and the % RS.

A scatter plot between a and % RS depicted in FIG. 15 shows a weak correlation and a greater uncertainty for the 30-35 and 50-55 groups. However, group 40 appears to have a stronger correlation. However, the five available data points do not warrant statistical significance. FIG. 15 shows two distinct data clusters similar to FIGS. 13 and 11 between the 30-40 and 50-55 groups. The overall behavior suggests that the $\alpha$ increases with decreasing overall % RS.

Table II of FIG. 16 summarizes the correlation coefficients produced from the above-described analyses. Using the different analysis techniques, the average propagating velocity of the AW2 appears to have a strong correlation among all three strength performance metrics. The velocity versus fiber strength has the highest correlation in the length groups 30-35 and 40, but relatively weaker in the length group 40. Nevertheless, all three analyses exhibit a similar overall correlation coefficient from 0.46 to 0.49. Energy attenuation versus different strength indicators appears to be much weaker. Length group 40, however, demonstrates a distinctively stronger correlation of the energy response to all three strength performance metrics.

Rayleigh Mode (AW2) Response to Average Compression Shell Strength. Compression test results are analyzed, and the average compression shell strength (ACS) is determined using linear scatter interpolation in the polar coordinate domain. The corresponding AW2 average propagating velocity squared and ACS values are compared in FIG. 17. Using the length grouping method, the analysis is conducted for each of the pole groups (30-35, 40, and 50-55). With the assumed linear regression model, the 30-35 pole group exhibits the highest correlation $R^2$ of approximately 0.37. The correlation performance reduces to 0.22 and nearly 0 for pole groups of 40 and 50-55. The strong linear correlation with the directly proportional relation suggests that a greater compression strength in the shell region tends to result in a higher propagating velocity of AW2. This finding is inconsistent in larger pole groups (40 and 50-55) which show a weaker correlation with different proportional relations.

Figure 17:
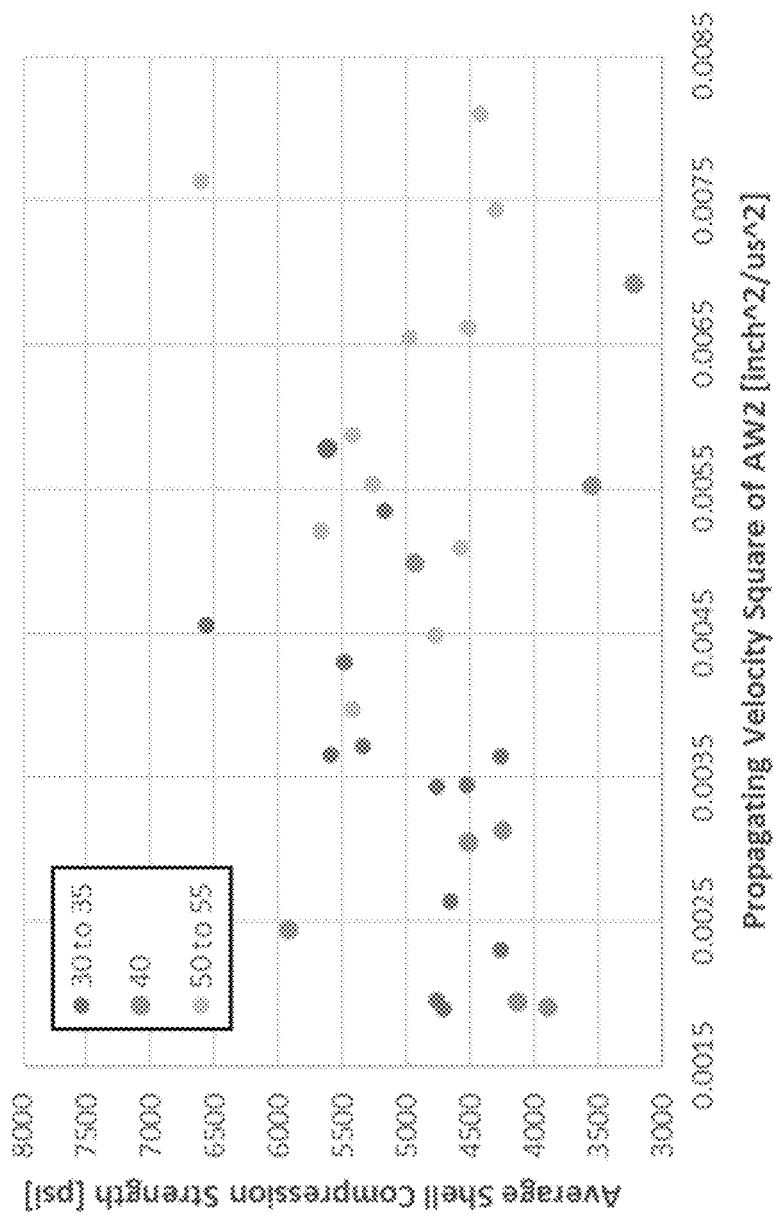
FIG. 17 is a graph of correlation between AW2 velocity square and ACS values determined from NDE testing of wooden specimen.
Figure 18:
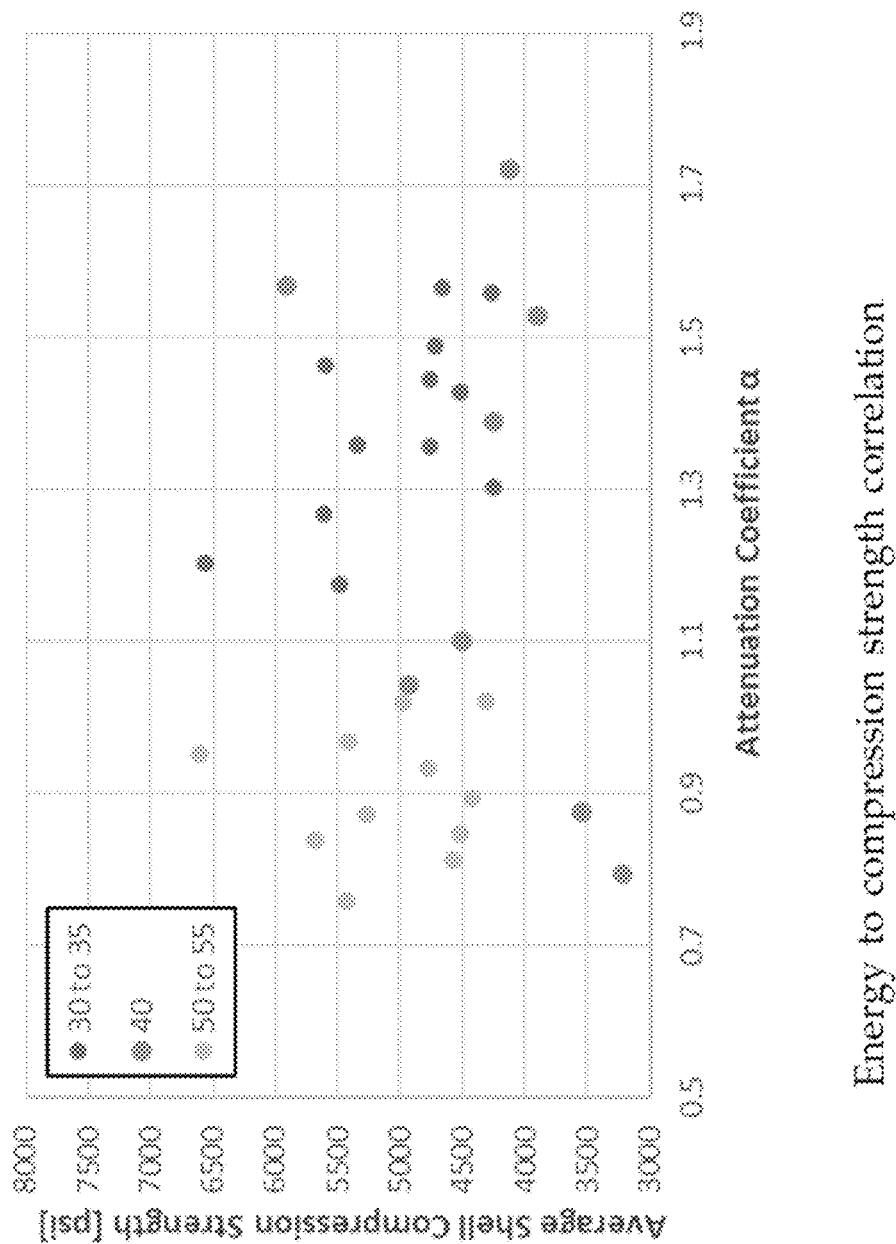
FIG. 18 is a graph of energy to compression strength correlation determined from NDE testing of wooden specimen.

Using an approach similar to that depicted in FIG. 17, peak energy responses in the form of the attenuation coefficient $\alpha$ are compared among the different pole groups. FIG. 18 shows the correlation performance of length groups 30-35, 40 and 50-55, respectively. Using the proposed logarithmic linear regression model, the correlation coefficients illustrate similar findings as shown in FIG. 14, with the 30-35 group exhibiting the highest correlation ($R^2=0.38$). The $R^2$ values decrease with increasing in pole length. The correlation coefficient of group 30-35 indicates an inversely proportional relation, supporting the conclusion that the acoustic wave tends to have a higher attenuation coefficient in wood with a weaker ACS strength.

Overall, the response of propagating speed and attenuation of AW2 to the ACS strength suggests a correlation if the pole length grouping method is used. A similar study was also performed when the species grouping method is used. Using the correlation coefficient as a metric of measurement, the length grouping method has a larger correlation coefficient than the species grouping method, suggesting a stronger overall dependency on the ultrasonic versus mechanical property correlation for the length group of 30-35. It is worth noting that the moisture content was assumed to be the same after the specimen are exposed to the controlled environment for 43 days. Since the poles were stored horizontally before the tests, the lateral moisture due to gravitational pull might have contributed to the inhomogeneous distribution of moisture on the test surface of each specimen. The proposed linear interpolation function for calculating the ACS values can be improved using a data-driven or physics-based model in future studies.

The technology disclosed herein presents a comparative analysis of examining the efficacy of the ultrasonic-based NDT. In an implementation, the technology correlates the fiber strength, the percentage remaining fiber strength, and the remaining pole strength to extracted ultrasonic wavefeatures including propagating velocity and the attenuation coefficient of the peak energy of AW2 through the standard static break test and compression testing. The result produces a significant overall correlation of 0.5 between the propagating velocity and the measured pole strength. It also resulted in an acceptable correlation level of 0.2 between the peak energy level and the measured pole strength.

The longitudinal compression test was conducted on the cross-sectional surfaces. Using a linear interpolator, the average shell compression strength values were calculated to compare corresponding AW2 characteristics. A stronger correlation appears in the length grouping method with a smaller pole length between 30 and 35 ($R^2 \approx 0.4$). In contrast, the species grouping method does not provide a conclusive result. However, the result can be improved if other interpolation schemes that are physics-driven and the contribution of moisture are included. Analysis of test results reveals the efficacy of the ultrasonic-based NDT for wood pole groundline characterization.

FIG. 19 illustrates a computing system 1601 suitable for implementing processing operations described herein related to NDE of a wooden specimen, with which aspects of the present disclosure may be practiced. Computing system 1601 may be implemented as a single apparatus, system, or device or may be implemented in a distributed manner as multiple apparatuses, systems, or devices. For example, computing system 1601 may comprise one or more computing devices that execute processing for applications and/or services over a distributed network to enable execution of processing operations described herein over one or more services. Computing system 1601 comprises, but is not limited to, processing system 1602, storage system 1603, software 1605, communication interface system 1607, and user interface system 1609. Processing system 1602 is operatively coupled with storage system 1603, communication interface system 1607, and user interface system 1609. Non-limiting examples of computer system 1601 comprise but are not limited to: smart phones, laptops, tablets, PDAs, desktop computers, servers, smart computing devices including television devices and wearable computing devices, e-reader devices, and conferencing systems, among other non-limiting examples. Other types of processing devices may be utilized as computer system 1601 without departing from the spirit of the present disclosure.

Processing system 1602 loads and executes software 1605 from storage system 1603. Software 1605 includes one or more software components 1606 that execute an NDE application/service for testing of a wooden specimen. In some examples, computing system 1601 may be a device that a user utilizes to interface with an NDE device via the NDE application/service for wooden specimen testing 1606. For example, computing device 1601, through execution of the NDE application/service for wooden specimen testing 1606, interfaces with an NDE device via a data transmission component of the NDE device where commands may be sent and signal data can be received. The computing device 1601 may interface with an NDE device via wired connection or wireless connection including any data transmission protocols as known to one skilled in the field of art. When executed by processing system 1602, software 1605 directs processing system 1602 to operate as described herein for at least the various processes, operational scenarios, and sequences discussed in the foregoing implementations, such as process 200. Computing system 1601 may optionally include additional devices, features, or functionality not discussed for purposes of brevity.

Computing system 1601 may further be utilized to control operation of NDE devices, for example, where a mode of operation of an NDE device may be managed through an exemplary NDE application/service executing on computing system 1601. For instance, a GUI of an NDE application/service may be configured to present user interface elements that enable users to toggle modes of operation of an NDE device that interface with computing system 1601. Examples of modes of operation of an NDE device comprise but are not limited to: a standby mode; a transmitting mode; a receiving mode; and a hybrid transmitting/receiving mode, among other examples. In instances where a computing system 1601 is transmitting commands to set an NDE device in one of the above-identified modes, commands may be transmitted to a processing unit of an NDE device that is configured to receive such commands via a data transmission component of the NDE device. As such, a computing device 1601 may be configured to implement a data transmission component that works with a same data transmission protocol that an NDE device is configured to receive data through. Moreover, computing system 1601 may further be configured to enable control parameters related to any aspect of NDE of wooden specimen, for example, through a GUI of an NDE application/service. This comprises but is not limited to: configuration of NDE devices; management of signal feasibility testing; management of parameters for NDE of wooden specimen; management and training of data modeling to assist with NDE analysis of acoustic signal data; network health analysis of a sample population of wooden specimen; generation of NDE reports including generation of customized NDE reports; and management of NDE reports (e.g., storage and transmission), among other examples.

Referring still to FIG. 19, processing system 1602 may comprise processor, a micro-processor and other circuitry that retrieves and executes software 1605 from storage system 1603. Processing system 1602 may be implemented within a single processing device but may also be distributed across multiple processing devices or sub-systems that cooperate in executing program instructions. Examples of processing system 1602 include general purpose central processing units, microprocessors, graphical processing units, application specific processors, sound cards, speakers, and logic devices, as well as any other type of processing devices, combinations, or variations thereof.

Storage system 1603 may comprise any computer readable storage media readable by processing system 1602 and capable of storing software 1605. Storage system 1603 may include volatile and nonvolatile, removable and non-removable media implemented in any method or technology for storage of information, such as computer readable instructions, data structures, program modules, cache memory or other data. Examples of storage media include random access memory, read only memory, magnetic disks, optical disks, flash memory, virtual memory and non-virtual memory, magnetic cassettes, magnetic tape, magnetic disk storage or other magnetic storage devices, or other suitable storage media, except for propagated signals. In no case is the computer readable storage media a propagated signal.

In addition to computer readable storage media, in some implementations storage system 1603 may also include computer readable communication media over which at least some of software 1605 may be communicated internally or externally. Storage system 1603 may be implemented as a single storage device but may also be implemented across multiple storage devices or sub-systems co-located or distributed relative to each other. Storage system 1603 may comprise additional elements, such as a controller, capable of communicating with processing system 1602 or possibly other systems. In some examples, storage system 1603 is a distributed network storage/web storage, where computing device 1601 is configured to connect to the distributed network storage/web storage via a network connection.

Software 1605 may be implemented in program instructions and among other functions may, when executed by processing system 1602, direct processing system 1602 to operate as described with respect to the various operational scenarios, sequences, and processes illustrated herein, such as process 200. For example, software 1605 may include program instructions for an NDE application/service for wooden specimen testing 1606, as described in the foregoing description.

In particular, the program instructions may include various components or modules that cooperate or otherwise interact to carry out the various processes and operational scenarios described herein. The various components or modules may be embodied in compiled or interpreted instructions, or in some other variation or combination of instructions. The various components or modules may be executed in a synchronous or asynchronous manner, serially or in parallel, in a single threaded environment or multi-threaded, or in accordance with any other suitable execution paradigm, variation, or combination thereof. Software 1605 may include additional processes, programs, or components, such as operating system software, virtual machine software, or other application software. Software 1605 may also comprise firmware or some other form of machine-readable processing instructions executable by processing system 1602.

In general, software 1605 may, when loaded into processing system 1602 and executed, transform a suitable apparatus, system, or device (of which computing system 1601 is representative) overall from a general-purpose computing system into a special-purpose computing system customized to process data and respond to queries. Indeed, encoding software 1605 on storage system 1603 may transform the physical structure of storage system 1603. The specific transformation of the physical structure may depend on various factors in different implementations of this description. Examples of such factors may include, but are not limited to, the technology used to implement the storage media of storage system 1603 and whether the computer-storage media are characterized as primary or secondary storage, as well as other factors.

For example, if the computer readable storage media are implemented as semiconductor-based memory, software 1605 may transform the physical state of the semiconductor memory when the program instructions are encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate the present discussion.

Communication interface system 1607 may include communication connections and devices that allow for communication with other computing systems (not shown) over communication networks (not shown). Communication interface system 1607 may also be utilized to cover interfacing between processing components described herein. Examples of connections and devices that together allow for inter-system communication may include network interface cards or devices, wired and/or wireless modules, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned media, connections, and devices are well known and need not be discussed at length here.

User interface system 1609 is optional and may include a keyboard, a mouse, a voice input device, a touch input device for receiving a touch gesture from a user, a motion input device for detecting non-touch gestures and other motions by a user, and other comparable input devices and associated processing elements capable of receiving user input from a user. Output devices such as a display, speakers, haptic devices, and other types of output devices may also be included in user interface system 1609. In some cases, the input and output devices may be combined in a single device, such as a display capable of displaying images and receiving touch gestures. The aforementioned user input and output devices are well known in the art and need not be discussed at length here.

User interface system 1609 may also include associated user interface software executable by processing system 1602 in support of the various user input and output devices discussed above. Separately or in conjunction with each other and other hardware and software elements, the user interface software and user interface devices may support a graphical user interface, a natural user interface, or any other type of user interface, for example, that enables front-end processing of exemplary application/services described herein (including an NDE application/service for wooden specimen testing 1606). A graphical user interface of user interface system 1609 may further be configured to display graphical user interface elements (e.g., data fields, menus, graphs, charts, data correlation representations and identifiers, control elements, real-time (or near real-time) testing data; waveform data, etc.) that are representations generated from processing ultrasonic signal data received from one or more NDE devices. For example, processing of received ultrasonic signal data, received from one or more NDE devices, may be utilized to provide explicit statistical data regarding a condition of a wooden specimen as well as classifications of a state of a wooden specimen that reflect algorithmic analysis of received ultrasonic signal data (e.g., that the wooden specimen is: tagged for replacement, flagged for re-testing at specified future time period; in good condition). Furthermore, as referenced above, data modeling of an exemplary NDE application/service is configured to enable projections to be provided for a wooden specimen (or a plurality of wooden specimen) where projections may relate to an estimated condition of a wooden specimen, recommendations for future management of wooden specimen and valuation of wooden specimen. As referenced in the foregoing description, valuation of wooden specimen, based on analysis provided herein, may comprise present valuations as well as future valuation projections. As referenced in the foregoing description, an exemplary GUI may further be configured to enable users to send control commands to control NDE of a wooden specimen. For example, commands may be transmitted to vary scientific parameters (e.g., voltage, resonance frequency) associated with NDE of a wooden specimen.

Communication between computing system 1601 and other computing systems (not shown), may occur over a communication network or networks and in accordance with various communication protocols, combinations of protocols, or variations thereof. Examples include intranets, internets, the Internet, local area networks, wide area networks, wireless networks, wired networks, virtual networks, software defined networks, data center buses, computing backplanes, or any other type of network, combination of network, or variation thereof. The aforementioned communication networks and protocols are well known and need not be discussed at length here. However, some communication protocols that may be used include, but are not limited to, the Internet protocol (IP, IPv4, IPv6, etc.), the transfer control protocol (TCP), and the user datagram protocol (UDP), Bluetooth, infrared, RF, cellular networks, satellite networks, global positioning systems, as well as any other suitable communication protocol, variation, or combination thereof.

In any of the aforementioned examples in which data, content, or any other type of information is exchanged, the exchange of information may occur in accordance with any of a variety of protocols, including FTP (file transfer protocol), HTTP (hypertext transfer protocol), REST (representational state transfer), WebSocket, DOM (Document Object Model), HTML (hypertext markup language), CSS (cascading style sheets), HTML5, XML (extensible markup language), JavaScript, JSON (JavaScript Object Notation), and AJAX (Asynchronous JavaScript and XML), as well as any other suitable protocol, variation, or combination thereof.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

Reference has been made throughout this specification to "one example" or "an example," meaning that a particular described feature, structure, or characteristic is included in at least one example. Thus, usage of such phrases may refer to more than just one example. Furthermore, the described features, structures, or characteristics may be combined in any suitable manner in one or more examples.

One skilled in the relevant art may recognize, however, that the examples may be practiced without one or more of the specific details, or with other methods, resources, materials, etc. In other instances, well known structures, resources, or operations have not been shown or described in detail merely to observe obscuring aspects of the examples.

While sample examples and applications have been illustrated and described, it is to be understood that the examples are not limited to the precise configuration and resources described above. Various modifications, changes, and variations apparent to those skilled in the art may be made in the arrangement, operation, and details of the methods and systems disclosed herein without departing from the scope of the claimed examples.

What is claimed is:

1. A method for performing non-destructive evaluation (NDE) of a wooden specimen, comprising, by a computing device, wherein the computing device is operatively coupled to a first acoustic wave transducer and a second acoustic wave transducer;
    receiving, by the first acoustic wave transducer, first acoustic wave signal data transmitted by the second acoustic wave transducer for NDE of the wooden specimen;
    receiving, by the second acoustic wave transducer, second acoustic wave signal data transmitted by the first acoustic wave transducer, wherein the second acoustic wave data is transmitted simultaneously with the first acoustic wave signal data;
    processing at least the first acoustic wave signal data to determine wave characteristics;
    determining an estimated strength metric of the wooden specimen based on one or more of the wave characteristics; and
    displaying, on a graphical user interface in communication with the computing device, an indication of the estimated strength metric of the wooden specimen.

2. The method of claim 1, wherein processing the acoustic wave signal data comprises identifying an AW2 wave based on detecting a peak energy of the acoustic wave signal data.

3. The method of claim 2, wherein the wave characteristics comprise one of an arrival velocity and an attenuation value of the AW2 wave.

4. The method of claim 3 where determining the estimated strength metric is based at least on an empirically determined correlation between the estimated strength metric and one of the arrival velocity and the attenuation value of the AW2 wave.

5. The method of claim 2 wherein processing the acoustic wave signal data further comprises performing a Gabor continuous wavelet transformation.

6. The method of claim 1 further comprising receiving second acoustic wave signal data of the wooden specimen corresponding to a second propagation plane different from a propagation plane of the acoustic wave signal data.

7. The method of claim 6 further comprising determining a moisture content of the wooden specimen based at least on the acoustic wave signal data and the second acoustic wave signal data.

8. The method of claim 1, wherein the acoustic wave signal data corresponds to an ultrasonic wave.

9. A computing device comprising:
    one or more computer-readable storage media;
    one or more processors operatively coupled with the one or more computer-readable storage media; and
    program instructions stored on the one or more computer-readable storage media that, when executed by the one or more processors, direct the computing device to at least:
        receive, by a first acoustic wave transducer, first acoustic wave signal data transmitted by a second acoustic wave transducer for non-destructive evaluation (NDE) of a wooden specimen, wherein the first acoustic wave transducer and the second acoustic wave transducer are operatively coupled to the computing device;
        receive, by the second acoustic wave transducer, second acoustic wave signal data transmitted by the first acoustic wave transducer, wherein the second acoustic wave signal data is transmitted simultaneously with the first acoustic wave signal data;
        process at least the first acoustic wave signal data to determine wave characteristics;
        determine an estimated strength metric of the wooden specimen based on one or more of the wave characteristics; and
        display, on a graphical user interface in communication with the computing device, an indication of the estimated strength metric of the wooden specimen.

10. The computing device of claim 9, wherein to process the acoustic wave signal data, the program instructions direct the computing device to identify an AW2 wave based on detecting a peak energy of the acoustic wave signal data.

11. The computing device of claim 10, wherein the wave characteristics comprise one of an arrival velocity and an attenuation value of the AW2 wave.

12. The computing device of claim 11, wherein the estimated strength metric is based at least on an empirically determined correlation between the estimated strength metric and one of the arrival velocity and the attenuation value of the AW2 wave.

13. The computing device of claim 10, wherein to process the acoustic wave signal data, the program instructions further direct the computing device to perform a Gabor continuous wavelet transformation.

14. The computing device of claim 9, wherein the program instructions further direct the computing device to receive second acoustic wave signal data of the wooden specimen corresponding to a second propagation plane different from a propagation plane of the acoustic wave signal data.

15. The computing device of claim 14, wherein the program instructions further direct the computing device to determine a moisture content of the wooden specimen based at least on the acoustic wave signal data and the second acoustic wave signal data.

16. One or more non-transitory computer-readable storage media having program instructions stored thereon that, when executed by one or more processors operatively coupled with the one or more non-transitory computer-readable storage media, direct a computing apparatus to at least:
receive, by a first acoustic wave transducer, acoustic wave signal data transmitted by a second acoustic wave transducer for non-destructive evaluation (NDE) of a wooden specimen, wherein the first acoustic wave transducer and the second acoustic wave transducer are operatively coupled to the computing apparatus;
process the acoustic wave signal data to determine wave characteristics, wherein to process the acoustic wave signal data, the program instructions direct the computing apparatus to identify an AW2 wave based on detecting a peak energy of the acoustic wave signal data;
determine an estimated strength metric of the wooden specimen based on one or more of the wave characteristics; and
display, on a graphical user interface in communication with the computing apparatus, an indication of the estimated strength metric of the wooden specimen.

17. The one or more non-transitory computer-readable storage media of claim 16, wherein the program instructions further direct the computing apparatus to receive, by the second acoustic wave transducer, second acoustic wave signal data transmitted by the first acoustic wave transducer, wherein the second acoustic wave signal data is transmitted simultaneously with the acoustic wave signal data.

18. The one or more non-transitory computer-readable storage media of claim 17, wherein the wave characteristics comprise one of an arrival velocity and an attenuation value of the AW2 wave.

19. The one or more non-transitory computer-readable storage media of claim 18, wherein the estimated strength metric is based at least on an empirically determined correlation between the estimated strength metric and one of the arrival velocity and the attenuation value of the AW2 wave.

20. The one or more non-transitory computer-readable storage media of claim 16, wherein the program instructions further direct the computing apparatus to receive second acoustic wave signal data of the wooden specimen corresponding to a second propagation plane different from a propagation plane of the acoustic wave signal data.

* * * * *